United States Patent
Argenta et al.

(10) Patent No.: US 7,216,651 B2
(45) Date of Patent: *May 15, 2007

(54) WOUND TREATMENT EMPLOYING REDUCED PRESSURE

(75) Inventors: Louis C. Argenta, Winston-Salem, NC (US); Michael J. Morykwas, Pfafftown, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/863,234

(22) Filed: May 23, 2001

(65) Prior Publication Data

US 2001/0029956 A1    Oct. 18, 2001

Related U.S. Application Data

(63) Continuation of application No. 09/026,353, filed on Feb. 19, 1998, which is a continuation of application No. 08/467,243, filed on Jun. 6, 1995, now abandoned, which is a continuation of application No. 08/028,677, filed on Mar. 9, 1993, now Pat. No. 5,636,643, which is a continuation-in-part of application No. 07/792,001, filed on Nov. 14, 1991, now Pat. No. 5,645,081.

(51) Int. Cl.
*A61B 19/00* (2006.01)

(52) U.S. Cl. ........................... 128/897; 602/42

(58) Field of Classification Search ........ 128/897–898; 602/42–53

See application file for complete search history.

(56) References Cited

U.S. PATENT DOCUMENTS 765,746 A    7/1904    Miner (Continued)

FOREIGN PATENT DOCUMENTS

DE          561757         10/1932

(Continued)

OTHER PUBLICATIONS

M. Gosta Arturson, *The Pathophysiology of Severe Thermal Injury*, JBCR, 6(2):129-146 (Mar.-Apr.) 1985.

(Continued)

*Primary Examiner*—John P. Lacyk
(74) *Attorney, Agent, or Firm*—Niels Haun; Dann, Dorfman, Herrell & Skillman, PC

(57) ABSTRACT

A method of treating tissue damage comprises applying a negative pressure to a wound sufficient in time and magnitude to promote tissue migration and thus facilitate closure of the wound. The method is applicable to wounds, burns, infected wounds, and live tissue attachments. A wound treatment apparatus is provided in which a fluid impermeable wound cover is sealed over a wound site. A screen in the form of an open-cell foam screen or a rigid porous screen is placed beneath the wound cover over the wound. A vacuum pump supplies suction within the wound cover over the treatment site.

125 Claims, 5 Drawing Sheets

U.S. PATENT DOCUMENTS

| | | |
|---|---|---|
| 774,529 A | 11/1904 | Nieschang |
| 843,674 A | 2/1907 | Funk |
| 1,355,679 A | 10/1920 | McConnell |
| 1,355,846 A | 10/1920 | Rannells |
| 1,385,346 A | 7/1921 | Taylor |
| 1,936,129 A | 11/1933 | Fisk |
| 2,025,492 A | 12/1935 | Aird |
| 2,195,771 A | 4/1940 | Estler |
| 2,232,254 A | 2/1941 | Morgan |
| 2,280,915 A | 4/1942 | Johnson |
| 2,338,339 A | 1/1944 | LaMere |
| 2,547,758 A | 4/1951 | Keeling |
| 2,969,057 A | 1/1961 | Simmons |
| 3,026,526 A | 3/1962 | Montrose |
| 3,026,874 A | 3/1962 | Stevens |
| 3,042,041 A | 7/1962 | Jascalevich |
| 3,115,138 A | 12/1963 | McElvenny |
| 3,115,318 A | 12/1963 | Caillette |
| 3,324,855 A | 6/1967 | Heimlich |
| 3,367,332 A | 2/1968 | Groves |
| 3,382,867 A | 5/1968 | Reaves |
| 3,478,736 A | 11/1969 | Roberts et al. |
| 3,481,326 A | 12/1969 | Schamblin |
| 3,486,504 A | 12/1969 | Austin, Jr. |
| 3,520,300 A | 7/1970 | Flower et al. |
| 3,568,675 A | 3/1971 | Harvey |
| 3,572,340 A | 3/1971 | Llyod et al. |
| 3,610,238 A | 10/1971 | Rich, Jr. |
| 3,682,180 A | 8/1972 | McFarlane |
| 3,713,622 A | 1/1973 | Dinger |
| 3,753,439 A | 8/1973 | Brugarolas et al. |
| 3,826,254 A | 7/1974 | Mellor |
| 3,874,387 A | 4/1975 | Barbieri |
| 3,896,810 A | 7/1975 | Akiyama |
| 3,908,664 A | 9/1975 | Loseff |
| 3,938,540 A | 2/1976 | Holbrook et al. |
| 3,954,105 A | 5/1976 | Nordby et al. |
| 3,978,855 A | 9/1976 | McRae et al. |
| 3,993,080 A | 11/1976 | Loseff |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,169,563 A | 10/1979 | Leu |
| 4,172,455 A | 10/1979 | Beaussant |
| 4,224,941 A | 9/1980 | Stivala |
| 4,224,945 A | 9/1980 | Cohen |
| 4,250,882 A | 2/1981 | Adair |
| 4,261,363 A | 4/1981 | Russo |
| 4,275,721 A | 6/1981 | Olson |
| 4,297,995 A | 11/1981 | Golub |
| 4,373,519 A | 2/1983 | Errede et al. |
| 4,382,441 A | 5/1983 | Svedman |
| 4,392,853 A | 7/1983 | Muto |
| 4,419,097 A | 12/1983 | Rowland |
| 4,452,845 A | 6/1984 | Lloyd et al. |
| 4,459,139 A | 7/1984 | vonReis et al. |
| 4,465,062 A | 8/1984 | Versaggi et al. |
| 4,469,092 A | 9/1984 | Marshall et al. |
| 4,475,909 A | 10/1984 | Eisenberg |
| 4,480,638 A | 11/1984 | Schmid |
| RE31,887 E | 5/1985 | Hodgson |
| 4,525,166 A | 6/1985 | Leclerc |
| 4,527,064 A | 7/1985 | Anderson |
| 4,540,412 A | 9/1985 | Van Overloop |
| 4,543,100 A | 9/1985 | Brodsky |
| 4,569,674 A | 2/1986 | Phillips et al. |
| 4,573,965 A | 3/1986 | Russo |
| 4,605,399 A | 8/1986 | Weston et al. |
| 4,608,041 A | 8/1986 | Nielsen |
| 4,624,656 A | 11/1986 | Clark et al. |
| 4,627,427 A | 12/1986 | Arco |
| 4,640,688 A | 2/1987 | Hauser |
| 4,655,754 A | 4/1987 | Richmond et al. |
| 4,661,093 A | 4/1987 | Beck et al. |
| 4,717,382 A | 1/1988 | Clemens et al. |
| 4,743,232 A | 5/1988 | Kruger |
| 4,753,231 A | 6/1988 | Lang et al. |
| 4,759,354 A | 7/1988 | Quarfoot |
| 4,764,167 A | 8/1988 | Tu |
| 4,765,316 A | 8/1988 | Marshall |
| 4,773,409 A | 9/1988 | Cilento et al. |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,851,545 A | 7/1989 | Song et al. |
| 4,860,737 A | 8/1989 | Lang et al. |
| 4,863,449 A | 9/1989 | Therriault |
| 4,875,473 A | 10/1989 | Alvarez |
| 4,878,901 A | 11/1989 | Sachse |
| 4,906,233 A | 3/1990 | Moriuchi et al. |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 5,035,884 A | 7/1991 | Song et al. |
| 5,071,403 A | 12/1991 | Larsson |
| 5,086,764 A | 2/1992 | Gilman |
| 5,100,396 A | 3/1992 | Zamierowski |
| 5,106,362 A | 4/1992 | Gilman |
| 5,113,871 A | 5/1992 | Viljanto |
| 5,149,331 A | 9/1992 | Ferdman et al. |
| 5,228,431 A | 7/1993 | Giarretto |
| 5,261,893 A | 11/1993 | Zamierowski |
| 5,636,643 A | 6/1997 | Argenta et al. |
| 5,645,081 A | 7/1997 | Argenta et al. |
| 6,551,317 B2 | 4/2003 | Berish et al. |

FOREIGN PATENT DOCUMENTS

| | | |
|---|---|---|
| DE | 847475 | 6/1952 |
| DE | 2809828 | 9/1978 |
| DE | 4111122 | 4/1993 |
| EP | 0620720 | 10/1994 |
| EP | 0688189 | 9/2000 |
| EP | 0688189 B2 | 6/2005 |
| GB | 641061 | 8/1950 |
| GB | 1273342 | 5/1972 |
| GB | 1457164 | 12/1976 |
| GB | 2195255 | 4/1988 |
| WO | 80/01139 | 6/1980 |
| WO | 87/00439 | 1/1987 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |

OTHER PUBLICATIONS

R. A.F. Clark et al., The Molecular and Cellular Biology of Wound Repair, Chapter 1 (1988).

Jeter, K.F. et al. (eds.), "Managing Draining Wounds and Fistulae: New and Established Methods," Chronic Wound Care: Health Management Publications, 1990, pp. 240-246.

Aeros, "Moblvac II."
Aeros, Aeros Instruments, Inc. 1111 Lakeside Drive, Gurnee, IL 60031. Aug. 1993. "Care-E-Vac."
Emerson, Series 55. J. H. Emerson Co., 22 Cottage Park Ave., Cambridge, MA 02140. "Emerson Post-Operative Suction Pumps."
Emerson, J. H. Emerson Co., (address: same as above). "Emerson Transport Suction Unit."
Aeros, Aeros Instruments, Inc. 3411 Commercial Ave., Northbrook, IL 60062. Oct. 1988. Part No. 1504-02 7M. "Instavac Aspirator."
"Pleur-evac. Adult-Pediatric, Non-Metered." Code Number: A-4000. Control No. F7961J.
Instruction Manual, Creative Medical Laboratories, Inc. P.O. Box 6347, Rochester, Minn. 55903. "TUGS" (Transportable Universal Gradient Suction).
Deknatel, Div. of Howmedia, Inc. Quenns Village, NY 11429. "Pleur-evac."
Sparta Instrument Corp. 26602 Corporate Ave., Hayward, CA 94545. "Power Source Multi-Purpose Surgical Aspirator."
Wells Johnson Company, 2045 N. Forbes Blvd., Suite 106, Tucson, AZ. "Point 5 Aspirator."
Microtek Heritage, Inc. P.O. Box 2487, Columbus, MS 39704. "Wound-Evac ET."
Fleischmann, W. *Wund Forum Spezial.* IHW '94. "Vakuumversiegelung zur Behandlung von Problemwunden" (with English translation: "Vacuum sealing for Treatment of Problematical Wounds."
Fleischmann, W. *Acta Orthopaedica Belgica*. vol. 58, Suppl. I-1992 "Treatment of Bone and Soft Tissue Defects in Infected Nonunion."
Fleischmann, W. *Unfall Chirurg.* Springer-Variag 1993. "Vakuumversiegelung zur Behandlung des Weichteilschadens bei offenen Frakturen." with English translation.
Valenta, A. *American Journal of Nursing.* Apr. 1994. "Using the Vacuum Dressing Alternative for Difficult Wounds."
Junod, "Hyperemia by Suction Apparatus" Chapter VIII.
Saunders, J. W., The Lancet, pp. 1286-1287, Jun. 28, 1952, "Negative-Pressure Device for Controlled Hypotension during Surgical Operations".
Landis et al, Robinette Foundation of the Hospital of the University of Pennsylvania, "The Effects of Alternate Suction and Pressure on Blood Flow to the Lower Extremities".
Hargens et al., Space Physiology Laboratory, Life Science Division, NASA Ames Research Center, "Control of Circulatory Function in Altered Gravitational Fields".
Wolthuis et al, Physiological Reviews, 54: 566-595, Jul. 1974, "Physiological Effects of Locally Applied Reduced Pressure in Man".
Viljanto et al., Br. J. Surg., 63: 427-430, 1976, "Local Hyperalimentation of Open Wounds".
Dillon, R. Angiology—The Journal of Vascular Diseases, pp. 47-55, Jan. 1986, "Treatment of Resistant Venous Stasis Ulcers and Dermatitis with the End-Diastolic Pneumatic Compression Boot".
Lundvall et al., Acta Physiol Scand, 136: 403-409, accepted Jan. 28, 1989, "Transmission of externally applied negative pressure to the underlying tissue. A study on the upper arm of man".
Klemp et al., The Journal of Investigative Dermatology, pp. 725-726 (1989), "Subcutaneous Blood Flow in Early Male Pattern Baldness".
A. Harle, Z. Orthop., 127: 513-517 (1989), "Schwachstellen herkommlicher Drainagen" with English Translation.
Dunlop et al., Br. J. Surg., 77: 562-563 (1990), "Vacuum drainage of groin wounds after vascular surgery: a controlled trail" with English Translation.
Maddin et al., International Journal of Dermatology, 29: 446-450 (1990), "The Biological Effects of a Pulsed Electrostatic Field with Specific Reference to Hair: Electrotrichogenesis".
Nakayama et al., Ann. Plast. Surg., 499-502 (1991), "A New Dressing Method for Free Skin Grafting in Hands".
Hargens et al., Aviation, Space and Environmental Medicine, pp. 934-937, Oct. 1991, "Lower Body Negative Pressure to Provide Load Bearing in Space".
Author Unknown, Science, Sep. 1992, p. 42, "The Not-So-Bald-Truth".

Techno Takatsuki Co., Ltd., 8-16 Hatchonishimachi, Takatsuki City, Osaka, Japan, "HiBlow Air Pump".
Wells Johnson Company, 2045 N. Forbe Blvd., Suite 106, Tucson, AZ, "Suction Tips".
Industrial Equipment News, P.O. Box 1158, Skokie, IL 60076-9786, "Miscellaneous Equipment".
Letsou et al. "Stimulation of Adenylate Cyclase Activity in Cultured Endothelial Cells Subjected to Cyclic Stretch." Cardiovascular Surgery 3. Toronto. Sep. 1989. 634-639.
Bucalo et al., "Inhibition of Cell Proliferation by Chronic wound Fluid." Wound Repair and Regeneration. Miami 1991. 181-186.
Falanga, Vincent. "Growth Factors and Chronic Wounds: The need to Understand the Microenvironment." Journal of Dermatology, Bol. 19: 667-672. 1992.
Urschel et al. "The Effect of Mechanical Stress on Soft and Hard Tissue Repair; a Review." British Journal of Plastic Surgery. 41, 182-186. 1988.
Gogia, Prem P. "The Biology of Wound Healing." Ostomy/Wound Management. Nov.-Dec. 1992. pp. 12-20.
Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68.
Olenius et al. "Mitotic Activity in Expanded Human Skin." Plastic and Reconstructive Surgery. Feb. 1993. 213-215.
Mulder, G. D. et al. (eds.), *Clinicians' Pocket Guide to Chronic Wound Repair*, (Spartanburg, SC: Wound Helaing Publications), 1991, pp. 54-55.
Chariker, M. E. et al. (eds), "Effective Management of Incisional and Cutaneous Fistulae with Closed Suction Wound Drainage," Contemporary Surgery, vol. 34, Jun. 1989, pp. 59-63.
Rastgeldi, S.: I. Pressure Treatment of Peripheral Vascular Diseases. II. Intermittent Pressure Treatment of Peripheral Vascular Diseases. Opuscula Medica, Suppl. XXVII, 1972.
OP-Journal Nr. 3, Jahr. 6, Dec. 1990, pp. 31-35 W. Fleischmann, M. Mentzel, L. Kinzl "BWS, Gefahren und Komplikationen der Therapie" with English Trans.
Zumtobel et al., (1991) "Wunddrainage in der Elektiveund Notfallchirurgie" Wolfgang Pabst Verlag, relevant p. 12, left column. English Translation attached.
Saechtling, Kunststoff-Taschenbuch, 24. Ausgabe 1989, S. 439, 477. English Translation attached.
Mutschler, W. Bakker D. J., "Temporarer Hautersatz", ZFA 1989, Heft 24, S. 714-720 als Sonderdruck. English Translation attached.
W. Fleischmann, U. Becker, M. Bischoff, H. Hoekstra, "Vacuum sealing: indication, technique, and results", Eur. J. Orthop & Traumato (1995) 5:37-40.
Argenta LC, Morykwas MJ. Vacuum-assisted closure: a new method for wound control and treatment: clinical experience. Ann Plast Surg 1997;38: 563-576.
Morykwas MJ, Argenta LC, Shelton-Brown EI, McGuirt W. Vacuum-assisted closure: a new method for wound control and treatment: animal studies and basic foundation. Ann Plast Surg 1997; 38:553-62.
Davydov IA, Larichev AB, Smirnov AP, Flegontov VB. Vakuumterapiia v lechenii ostrykh gnoinykh zabolevanii miagkikh tkanei i gnoinykh ran. [Vacuum therapy of acute suppurative diseases of soft tissues and suppurative wounds]. Russian Vestnik Khirurgii Imeni i—i—Grekova 1988; 141: 43-6 with Eng. Trans.
Davydov IA, Abramov AI, Larichev AB. Vakuum-terapiia v preduprezhdenii posleoperatsionnoi ranevoi infektsii. [Vacuum therapy in the prevention of postoperative wound infection]. Russian Vestnik Khirurgii Imen i—i—Grekova 1991; 147:91-5, with English Translation.
Iankov NI. Simuliatsiia konsolidatsii perelomov nizhnei cheliusti vaktuumnoi terapiei. [Stimulation of consolidation of mandibular fractures by means of vacuum therapy] Russian. Stomatologiia 1971; 50: 86, with Eng. Trans.
Inoiatov IM, Aleksandrov VB. Lechenie promezhnostnoi rany posle amputatsii priamoi kishki vakuum-aspiratsiei. [Vaccum aspiration in the treatment of the perineal wound following extirpation of the rectum]. Russian. Khirurgiia 1971; 47: 74-8, with English Translation.

Kochnev VA. Primenenie vakuum-drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian. Voprosy Onkologii 1967; 13:102-5, w/Eng. Trans.

Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia i Protezirovanie 1966;27:19-22, with English Translation.

Mirazimov BM, Vasina TA, Mezhericher MI. Mikroflora dlitel'no nekazhivaiushchikh ran i effektivnost' metoda vakuumirovaniia. [Microflora of prolonged non-healing wounds and the effectiveness of the vacuum evaporative method]. Russian. Khirurgiia 1967; 43: 40-3, with English Translation.

Mirazimov BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967; 14:224-30, with Eng. Translation.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411-5, w/Eng. Trans.

Volkov LA. Ispol'zovanie vakuum-drenazhnoi sistemy v khirurgicheskoi praktike. [Use of vacuum-drainage system in surgical practice]. Russian. Klinicheskaia Khirurgiia. 1973;7:54-5, with English Translation.

Teder H, Sanden G, Svedman P. Continuous Wound Irrigation in the Pig. J Invest Surg 1990;3:399-407.

Nakayama Y, Tomotari I, Soeda S. A New Method for the Dressing of Free Skin Grafts. Plast Reconstr Surg 1990;86:1216-1219.

Nakayama Y, Soeda S. A New Method for Free Skin Grafting in Hands. Ann Plast Surg 1991;26:499-502.

Fleischmann W, Strecker W, Bombelli M, Kinzl L. [Vacuum sealing as treatment of soft tissue damage in open fractures]. [German] Unfallchirurg 1993;96:488-92.

Brock WB, Barker DE, Burns RP. Temporary Closure of open abdominal wounds: the vacuum pack. Amer Surg 1995;61:30-5.

Shein M, Saadia R, Jameson JR, Decker GAG. The "sandwhich technique" in the Management of the Open Abdomen. Br J Surg 1986;73:369-70.

Broome A. Hansson L, Lundgren F, Smedberg S. Open Treatment of Abdominal Septic Catastrophies. World J. Surg 1983;7:792-6.

Valenta AL. Using the vacuum dressing alternative for difficult wounds. American Journal of Nursing 1994;94:44-5.

Vatanasapt V, Areemit S, Jeeravipoolvarn P, et al. Red rubber bulb, cheap and effective vacuum drainage. Journal of the Medical Association of Thailand 1989;72:193-7.

Brummelkamp WH, Taat CW, Slors JF. High-vacuum drainage and primary perineal wound closure in abdominoperineal excision of the rectum. Netherlands Journal of Surgery 1991;43:236-9.

Morykwas J, Argenta LC. Nonsurgical modalities to enhance healing and care of soft tissue wounds. Journal of the Southern Orthopaedic Association 1997;6:279-88.

Sames CP. Sealing of wounds with vacuum drainage [letter] Br Med J 1977;2:1123.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255.

Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554.

Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3.

Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.

Genecov DG, Schneider AM, Morykwas MJ, et al. A Controlled subatmospheric pressure dressing increases the rate of skin graft donor site reepithelialization. Ann Plast Surg 1998;40:219-25.

Mendez-Eastman S. Negative pressure wound therapy. Plastic Surgical Nursing 1998;18:27-9.

Banwell P. Withey S, Holten I. The use of negative pressure to promote healing [letter; comment]. Brit J Plast Surg 1998;51:79.

Blackburn J H Boemi L, Hall WWW. et al. Negative-pressure dressings as a bolster for skin grafts. Ann Plast Surg 1998;40:453-7.

Smith LA, Barker DE, Chase CW, et al. Vacuum Pack Technique of Temporary Abdominal Closure: A Four-Year Experience. Amer Surg 1997;63:1102-8.

McCulloch JM, Kemper CC. Vacuum-Compression Therapy for the Treatment of an Ischemic Ulcer. Physical Therapy 1998;73:165-9.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9.

Mirazimov, B.M.: Free Skin Grafting of Wounds and Ulcers using the "Vacuum Treatment" Method. [Citation data not given, pp. 54-58.] with English Trans.

Greer, Steven E., "Whither Subatmospheric Pressure Dressing?" The Institute of Reconstructive Plastic Surgery, The New York University Medical Center, New York, NY Apr. Issue of Annals of Plastic Surgery.

Registration No. 1982349. Owner, KCI Inc., 3440 E. Houston Street San Antonio TEXAS 78219. Source: United States Patent and Trademark Office official website. Filing date May 1, 1995 Registration Date Jun. 25, 1996.

Hidden Interest—A Special Report.; When Physicians Double as Entrepreneurs. The New York Times. p. 1. Nov. 30, 1999.

Defranzo, Anthony J., et al., "Vacuum-Assisted Closure for the Treatment of Degloving Injuries." Plastic and Reconstructive Surgery 104(7) 2145-48: (1999).

Morykwas, Michael J., et al., "Use of Subatmospheric Pressure to Prevent Progression of Partial-Thickness Burns in a Swine Model", Journal of Burn Care & Rehabilitation 20 (1 Part 1): 15-21 (1999).

Morykwas, Michael J., et al., "Use of Subatmospheric Pressure to Prevent Doxorubicin Extravasation Ulcers in a Swine Model". Journal of Surgical Oncology 72:14-17 (1999).

Molnar, Joseph A., et al., "Single-Stage Approach to Skin Grafting the Exposed Skull". Plastic and Reconstructive Surgery 105(1): 174-177 (2000).

Schneider, Andrew M., et al., "A New and Reliable Method of Securing Skin Grafts to the Difficult Recipient Bed". Plastic and Reconstructive Surgery 102(4) 1195-98 (1998).

Rosser, Charles J., et al., "A New Technique to Manage Perineal Wounds". Infections in Urology 13(2) 45-47 (2000).

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-50 (1999).

Meara, John G., et al., "Vacuum-Assisted Closure in the Treatment of Degloving Injuries". Annals of Plastic Surgery 42(6) 589-594 (1999).

Obdeijn, Miryam C., et al., "Vacuum-Assisted Closure in the Treatment of Poststernotomy Mediastinitis". Ann Thorac Surgery 68 2358-60 (1999).

Mendez-Eastman, Susan., "When wounds won't heal". RN 20-24 (1998).

Hartnett, Jacqueline M., "Use of Vacuum-Assisted Wound Closure in Three Chronic Wounds". JWOCN 25 (6) 281-290 (1998).

Mendez-Eastman, Susan., "Use of Hyperbaric Oxygen and Negative Pressure Therapy in the Multidisciplinary Care of a Patient with Nonhealing Wounds". JWOCN 26(2) 67-76 (1999).

Wooding-Scott, Margaret et al., "No-Wound is Too Big For Resorceful Nurses". RN, Dec. 1988, 22-25.

Davydov, et al., "Pathenogenic mechanism of the effect of vacuum therapy on the course of the wound process". Khirurgiia, Jun. 1990 (with English translation).

Davydov, et al., "Vacuum therapy in the treatment of suppurative lactation mastitis". Vestn. Khir., Nov. 1986 (with English translation).

Davydov, et al., "Bacteriological and cytological evaluation of the vacuum therapy of suppurative wounds". Vestn. Khir., Oct. 1988 (with Englsih translation).

Davydov, et al., "Basis of the use of forced early secondary suture in the treatment of suppurative wounds by the vacuum therapy method". Vestn. Khir., Mar. 1990 (with English translation).

Borzov, et al., "Vacuum therapy of some skin diseases". Vestn. Dermatol. Venerol., Aug. 1965 (with English translation).

Bier A. "Hyperemia by suction apparatus", Hyperemia as a Therapeutic Agent, Chicago, IL, Roberts Publishing; 1905: 74-85.

M.J. Morykwas and L.C. Argenta, "Techniques in Use of V.A.C. Treatment (in English)", Acta Chir. Austriaca Supplement Nr. 150, 1998, p. 3-4.

Garcia-Rinaldi, et al., "Improving the Efficiency of Wound Drainage Catheters", source not known, 1975, pp. 372-373.

Raffl, et al. "The Five Year Survival Rate for Gastric Cancer: Statistical Study from Syracuse Medical Center", Cancer, 6:756-759, Jul. 1953.

Raffl, et al., The Use of Negative Pressure Under Skin Flaps After Radical Mastectomy, Ann. Surg. 136: 1048, Dec. 1952.

Marie Knight, "A Second Skin for Patients with Large Drainage Wounds," Nursing 6(1) p. 37, 1976.

Oscar Ramirez, "Optimal Wound Healing under Op-Site Dressing" Plas. & Recon. Surg., 73(3): 474; 1984.

Helen Bibleheiner, "Dealing with a Wound that Drains 1.5 Liters per Day," RN Aug. 1986.

Peter Schwab, "Primary Closure of the Perineal Wound After Proctectomy" Mayo Clin. Proc., Mar. 1974, vol. 49.

Interlocutory Decision in Opposition proceedings in favor of patentee (Wake Forest—Argenta, et al.) dated Feb. 17, 2003.

Letter Supplemental to Notice of Opposition to European Patent No. 0688189 dated Nov. 12, 2002.

Notice of Opposition to European Patent No. 0688189 dated Jun. 12, 2001.

Opposer's Appeal from Interlocutory Decision—dated Jul. 4, 2003.

Communication from EPO, Summons to Attend Oral Proceedings Pursuant to Rule 71(1) EPC, European Patent 0,620,720, 6 pages, Dec. 8, 2003.

Avery, C., et al., "Negative pressure wound dressing of the radial forearm donor site", International Journal of Oral Maxillofacial Surgery, 2000; 29, pp. 198-200.

Armstrong, David G., et al., "Outcomes of Subatmospheric Pressure Dressing Therapy on Wounds of the Diabetic Foot", Ostomy/Wound Management 2002; 48(4): 64-68.

Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410.

Catarino, Pedro A., et al., "High-Pressure Suction Drainage via a Polyurethane Foam in the Management of Poststernotomy Mediastinitis", Ann Thorac Surg 2000; 70:1891-5.

Clinical Management Extra, Negative Pressure Therapy, Advances in Skin & Wound Care, Nov./Dec. 2001, vol. 14, No. 6, p. 321-322.

Cooper, Susan Mary, "Topical negative pressure in the treatment of pressure ulcers", Letters posted in the Journal of the American Acad of Dermatology, Aug., Part 1, 1999, p. 280.

Davydov, I.A., et al., "Concept of clinico-biological control of the wound", Vestnik khirurgii imeni I.I. Grekova, v. 146, issue 2, 1991, 132-6 (with English translation).

de la Torre, Jorge I., MD, et al., "Healing a Wound with an Exposed Herrington Road: A Case Study", Ostomy Wound Management, pp. 18-19, May 2002, vol. 48, Issue 5.

de Lange, M.Y., et al., "Vacuum-assisted closure: indications and clinical experience", Eur J Plast Surg (2000) 23:178-182.

Deva, Anand, K., et al., "Topical negative pressure in wound management", MJA, Vo. 173, pp. 128-131, Aug. 7, 2000.

Elwood, Eric T., et al., "Negative-Pressure Dressings in the Treatment of Hidradenitis Suppurativa", Ann Plast Surgery Jan. 2001; 46:49-51.

Evans, D. and Land, L., "Topical negative pressure for treating chronic wounds: a systematic review", British Journal of Plastic Surgery (2001), 54, 238-242.

Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143.

Fenn, C.H. and Butler, P.E.M., "Abdominoplasty wound-healing complications: assisted closure using foam suction dressing", British Journal of Plastic Surgery (2001), 54, 348-351.

Giovannini, Uberto M., MD, "Negative Pressure for the Management of an Exposed Vascular Dacron Polyester Patch", Annals of Plastic Surgery, 47(5): 577-578, 2001.

Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002.

Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554.

Hersh, Robert E., MD, et al., "The Vacuum-Assisted Closure Device as a Bridge to Sternal Wound Closure", Ann Plast Surg. 2001; 466: 250-254.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171.

Iusupov, I.N., et al., "Active drainage of a wound", Izdatelstvo Meditsina, St. Petersburg, Apr. 1987; 138(4):42-6 (with English Translation).

Joseph, Emmanuella, MD, et al., "A Prospective Randomized Trial of Vacuum-Assisted Closure Versus Standard Therapy of Chronic Nonhealing Wounds", WOUNDS 2000: 12(3): 60-67.

Josty, I.C., et al., "Vacuum-assisted closure: an alternative strategy in the management of degloving injuries of the foot", British Journal of Plastic Surgery (2001), 54, pp. 363-365.

Kostiuchenok, B.M., et al., "Vacuum Treatment in the Surgical Management of Suppurative Wounds", Izdatelstvo Meditsina, St. Petersburg, Sep. 1986; 137(9): 18-21 (with English Translation).

Kovacs, Laszlo H., MD, "Necrotizing Fasciitis", Annals of Plastic Surgery, vol. 47, No. 6, Dec. 2001, pp. 680-682.

Kranser, Diane L., "Managing Wound Pain in Patients with Vacuum-Assisted Closure Devices", Ostomy Wound Management 2002; 48(5): 38-43.

Mendez-Eastman, Susan, RN, CPSN, CWCN, "Guidelines for Using Negative Pressure Wound Therapy", Advances in Skin & Wound Care, vol. 14, No. 6, pp. 314-320, Nov./Dec. 2001.

Mendez-Eastman, Susan, RN, CPSN, CWCN, "wound therapy", Nursing2002, vol. 32, No. 5, May, pp. 59-63.

Mooney, James F., III., "Treatment of Soft Tissue Defects in Pediatric Patients Using the V.A.C. TM System", Clinical Orthopedics and Related Research, No. 376, pp. 26-31, Jul. 2000.

Scheufler, O., et al., "Problem-adapted application of vacuum occlusion dressings: case report and clinical experience", Eur J. Plast Surg (2000) 23: 386-390.

Sposato, G., et al., "Ambulant vacuum-assisted closure of skin-graft dressing in the lower limbs using a portable mini-VAC device", British Journal of Plastic Surgery (2001), 54, 235-237.

Tang, Augustine T.M., et al., "Novel application of vacuum assisted closure technique to the treatment of sternotomy wound infection", European Journal of Cardio-Thoracic Surgery 17 (2000) 482-484.

Wu, S.H., et al., "Vacuum therapy as an intermediate phase in wound closure: a clinical experience", Eur J Surg (2000) 23:174-177.

Zhivotaev VM. Vacuum therapy of postoperative infected wounds of the urinary bladder, Klinicheskaia Khiurgiia. 1970;5:36-39. (in Russian).

The Kremlin Papers . . . perspectives in wound care, "A collection of published studies complementing the research and innovation of wound care", Russian Medical Journal "Vestnik Khirurgii", 5 Russian Articles from 1986-1991, translated by BlueSky Medical Group Inc. © 2004.

Interlocutory decisions in Opposition proceedings in favor or patentee (Wake Forest—Argenta, et al.) dated May 19, 2004.

*Kinetic Concepts, Inc., et al.* vs. *Bluesky Medical Corporation, et al.*; Civil Action No. SA 03 CA 0832: Plaintiff's Original Complaint dated Aug. 28, 2003.

*Kinetic Concepts, Inc., et al.* vs. *Bluesky Medical Corporation, et al.*; Civil Action No. SA 03 CA 0832: Plaintiff's First Amended Complaint dated Sep. 8, 2003.

*Kinetic Concepts, Inc., et al.* vs. *Bluesky Medical Corporation, et al.*; Civil Action No. SA 03 CA 0832: Defendant BlueSky Medical Corporation's Original Answer to Plaintiff's First Amended Compliant dated Sep. 30, 2003.

*Kinetic Concepts, Inc., et al.* vs. *Bluesky Medical Corporation, et al.*; Civil Action No. SA 03 CA 0832: Answer, Additional Defenses, Counterclaims and Jury Demand of Medela, Inc. (Response due: Oct. 27, 2003—20 days after service) dated Oct. 6, 2003.

*Kinetic Concepts, Inc., et al.* vs. *Bluesky Medical Corporation, et al.*; Civil Action No. SA 03 CA 0832: Plaintiff's Reply to Defendant BlueSky Medical Corporation's Counterclaim dated Oct. 23, 2003.

*Kinetic Concepts, Inc., et al.* vs. *Bluesky Medical Corporation, et al.*; Civil Action No. SA 03 CA 0832: Summary of Appendix in Support of Medela AG's Motion to Dismiss for Lack of Personal Jurisdiction or, Alternatively, to Dismiss for Failure to State a Claim and for Partial Summary Judgment dated Oct. 24, 2003.

*Kinetic Concepts, Inc., et al.* vs. *Bluesky Medical Corporation, et al.*; Civil Action No. SA 03 CA 0832: Original Answer of Defendant Patient Care Systems, Inc., dated Oct. 7, 2003.

*Kinetic Concepts, Inc., et al.* vs. *Bluesky Medical Corporation, et al.*; Civil Action No. SA 03 CA 0832: Medela AG's Motion to Dismiss for Lack of Personal Jurisdiction or Alternatively, to Dismiss for Failure to State a Claim and For Partial Summary Judgment dated Oct. 24, 2003.

*Kinetic Concepts, Inc., et al.* vs. *Bluesky Medical Corporation, et al.*; Civil Action No. SA 03 CA 0832: Plaintiff's Reply to Defendant Medela, Inc.'s Counterclaim dated Oct. 27, 2003.

*Kinetic Concepts, Inc., et al.* vs. *Bluesky Medical Corporation, et al.*; Civil Action No. SA 03 CA 0832: Plaintiff's Response to Medela AG's Motion to Dismiss for Lack of Personal Jurisdiction, Motion to Dismiss for Failure to State a Claim, and Motion for Partial Summary Judgement, dated Nov. 10, 2003.

Davies, J.W.L, "Synthetic materials for covering burn wounds: Progress towards perfection. Part I. Short term dressing materials", Burns, Nov. 1983;10(2), 94-103.

Lamke, L.O., et al., "The evaporative water loss from burns and the water-vapour permeability of grafts and artificial membranes used in the treatment of burns", Burns, 3, 159-165, 1977.

Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381.

Alper, J., et. al., "Moist wound healing under a vapor permeable membrane", Journal of the American Academy of Dermatology, vol. 8, No. 3, Mar. 1983, pp. 347-353.

James, J.H., et. al. "The use of Opsite, A Vapour Permeable Dressing, on Skin Donor Sites", British Journal of Plastic Surgery (1975), 28, 107-110.

Nahas, L.F., et al., "Use of Semipermeable Polyurethane Membrane for Skin Graft Dressings", Plastics and Reconstructive Surgery, Jun. 1981, pp. 791-792.

Edlich, R.F., et al., "Surgical Devices in Wound Healing Management", Wound Healing Biochemical & Clinical Aspects, W.B. Saunders Company, © 1992, pp. 581-599.

Orr, RK, et al., "Early Discharge After Mastecomy. A Safe Way of Diminishing Hospital Cost", Am. Surg. Mar. 1987; 53(3) Abstract.

Otolaryngology, Head and Neck Surgery, The C.V. Mosby Company, © 1986, pp. 1716, 1724, and 2521.

Otolaryngology, vol. III, Head and Neck, W.B. Saunders Company, © 1980, pp. 2963.

Lore, Jr., J.M., "An Atlas of Head and Neck Surgery", Second Edition, vol. II, W.B. Saunders Company, © 1973.

Murray, Y., "Tradition Rather Than Cure", Wound Care, Nursing Times, Sep. 21, vol. 94, No. 38, 1988 (with German translation).

Alper, Joseph C., et al., "The In Vitro Response of Fibroblasts to the Fluid that Accumulates Under a Vapor-Permeable Membrane". Journal of Investigative Dermatology, 84:513-515, 1985.

Alper, Joseph C., et al., "Use of the Vapor Permeable Membrane for Cutaneous Ulcers: Details of application and side effects", Journal of the American Academy of Dermatology, vol. 11, No. 5, Part I, Nov. 1984, pp. 858-866.

Angermeier, Marla C., et al., "Vapor-Permeable Membrane Therapy for Ulcers of Osteomyelitis", J. Dermatol. Surg. Oncol,, 10:5, May 1984, pp. 384-388.

Bourke, et al., "Comparison Between Suction and Corrugated Drainage After Simple Mastectomy: A Report on Controlled Trial", Br. J. Surg., vol. 63, 1976, pp. 67-69.

Eaglstein, William H., "Experiences with Biosynthetic Dressings", Journal of the American Academy of Dermatology, vol. 12, No. 2, Part 2, Feb. 1985, pp. 434-440.

Falanga, Vincent, et al., "A Therapeutic Approach to Venous Ulcers", Journal of the American Academy of Dermatology, vol. 14, No. 5, Part 1, May 1986, pp. 777-784.

Friedman, S., et al., "Treatment of Dermabrasion Wounds with a Hydrocolloid Occlusive Dressing", Arch Dermatol, vol. 121, Dec. 1985, pp. 1486-1487.

Friedman, Stephen J., et al., "Management of Leg Ulcers with Hydrocolloid Occlusive Dressing", Arch. Dermatol., vol. 120, Oct. 1984, pp. 1329-1336.

Holland, K.T., et al., "A Comparison of the In Vivo Antibacterial Effects of OpSite, Tegaderm and Ensure dressings", Journal of Hospital Infection, 1985, 6, pp. 299-303.

Jeter, Katherine F., et al., "Wound Dressings of the Nineties: Indications and Contraindications", Clinics in Podiatric Medicine and Surgery, vol. 8, No. 4, Oct. 1991, pp. 799-816.

Katz, Stuart, et al., "Semipermeable Occlusive Dressings", Arch Dermatol., vol. 122, Jan. 1986, pp. 58-62.

Lewis, R.T., "Knitted Polypropylene (Marlex) Mesh in the Repair of Incisional Hernias", The Canadian Journal of Surgery, vol. 27, No. 2, Mar. 1984, pp. 155-157.

Satas, Donatas, "Handbook of Pressure-Sensitive Adhesive Technology", Silicone Release Coatings, Van Nostand Reinhold Company, 1982, pp. 384-402.

Turner, T.D., "A Look at Wound Dressings", Health and Social Service Journal, May 4, 1979, pp. 529-531.

Turner, T.D., et al., "Wound Management Product Selection", Journal of Sterile Services Management, Apr. 1985, pp. 3-6.

Varghese, Mathew C., et al., "Local Environment of Chronic Wounds Under Synthetic Dressings", Arch. Dermatol, vol. 122, Jan. 1986, pp. 52-57.

Viljanto, J., "Cellstic: A Device for Wound Healing Studies in Man. Description of the Method", Journal of Surgical Resrach, 20, 1976, pp. 115-199.

Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236-239.

Wilson, John L., et al., "Loss of Blood Volume in Spinal Surgery with Use of Closed Wound Suction: An Experimental Study", Southern Medical Journal, Jul. 1968, pp. 761-763.

Swearingen, Pamela L., The Addison Wesley Photo-Atlas of Nursing Procedures—Administering Medications and Monitoring Fluids—Managing Gastrointestinal Procedures—Managing Gastri Tubes, Copyright 1984.

Dewan, P.A., et al., "An Alternative Approach To Skin Graft Donor Site Dressing", Aust. N.Z. J. Surg. 1986, 56, 509-510.

Kohlman, P., et al., "Pouching Procedure To Collect Drainage From Around A Biliary Drainage Catheter", Ostomy/Wound Management, Nov./Dec. 1991, pp. 47-50, V. 37.

Alper, J., "Recent Advances in Moist Wound Healing", Southern Medical Journal, Nov. 1986, pp. 1398-1404, V. 79, N.11.

Untitled Article, The Lancet, Jun. 14, 1952, pp. 1175-1176.

Putney, F., "The Use of Continuous Negative Pressure After Laryngectomy and Radical Neck Dissection", Surgery, Gynecology & Obstetrics, Aug. 1956, pp. 244-246.

Pleupump MK II, printouts from websites, www.xenamedical.se and www.landstingnet.sormland.se, Aug. 14, 2001 (12 pages).

Brummelkamp, W., et al., "High-vacuum Drainage and Primary Perineal Wound Closure in Abdominoperineal Excision of the Rectum", The Netherland Journal of Surgery, 1991, pp. 236-239, V. 43, No. 6.

Engdahl, O., et al., "Quantification of Aspirated Air Volume Reduces Treatment Time in Pneumothorax", Eur Respir J., 1990, 3, pp. 649-652.

Spengler, M., et al., "Performance of Filtered Sump Wound Drainage Tubes", Surgery, Gynecology & Obstetricsq, Mar. 1982, pp. 333-336, vol. 154.

Hallstrom, B., et al., "Postoperative Course After Total Hip Arthroplasty: Wound Drainage Versus No Drainage", Orthopaedic Review, Jul. 1992, pp. 847-851.

Miles, W., et al., "A Method of Performing Abdominoperineal Excision for Carcinoma of the Rectum and of the Terminal Portion of the Pelvic Colon", The Lancet, Dec. 19, 1908, pp. 1812-1813.

Benjamin, P., "Faeculent Peritonitis: A Complication of Vacuum Drainage", Br. J. Surg., 1980, pp. 453-454, vol. 67.

Sagi, A., et al., "Burn Hazard From Cupping—An Ancient Universal Medication Still in Practice", Burns, 1988, pp. 323-325, vol. 14, No. 4.

Agrama, H., et al., "Functional Longevity of Intraperitoneal Drains", The American Journal of Surgery, Sep. 1976, pp. 418-421, vol. 132.

Magee, C., et al., "Potentiation of Wound Infection by Surgical Drains", The American Journal of Surgery, May 1976, pp. 547-549, vol. 131.

Birdsell, D., et al., "The Theoretically Ideal Donor Site Dressing",Annals of Plastic Surgery, Jun. 1979, pp. 535-537, vol. 2, No. 6.

Cruse, P., et al., "A Five-Year Prospective Study of 23,649 Surgical Wounds", Surgical Wounds/Cruse and Foord, Aug. 1973, pp. 206-210, vol. 107.

Aubrey, D., et al., "Treatment of the Perineal Wound After Proctectomy by Intermittent Irrigation", Arch. Surg., Oct. 1984, pp. 1141-1144, vol. 119.

Mayo, C., "The One-Stage Combined Abdominoperineal Resection for Carcinoma of the Rectum, Rectosigmoid and Sigmoid", Surgical Clinics of North America, Aug. 1939, pp. 1011-1019.

Draper, J., "Make the dressing fit the wound", Nursing Times, Oct. 9, 1985, pp. 32-35.

Schumann, D., et al., "Preoperative Measures to Promote Wound Healing", Nursing Clinics of North America, Dec. 1979, pp. 683-699, vol. 14, No. 4.

Besst, J., et al., "Wound-Healing—Intraoperative Factors", Nursing Clinics of North America, Dec. 1979, pp. 701-711, vol. 14, No. 4.

Cooper, D., et al., "Postsurgical Nursing Intervention as an Adjunct to Wound Healing", Nursing Clinics of North America, Dec. 1979, pp. 713-725, Nursing Clinics of North America, vol. 14, No. 4.

O'Byrne, C., "Clinical Detection and Management of Postoperative Wound Sepsis", Nursing Clinics of North America, Dec. 1979, pp. 727-741, vol. 14, No. 4.

Keith, C., "Would Management Following Head and Neck Surgery", Nursing Clinics of North America, Dec. 1979, pp. 761-778, vol. 14, No. 4.

Tenta, L., et al., "Suction Drainage of Wounds of the Head and Neck", Surgery, Gynecology. & Obstetrics, Dec. 1989, p. 558, vol. 169.

Firlit, C., et al., "Surgical Wound Drainage: A Simple Device for Collection", journal of Urology, Aug. 1972, pp. 327, vol. 108.

Worth, M., et al., "The Effectiveness of Bacterial Filtration in Vented Wound Drains", Journal of Surgical Research, 1979, pp. 405-407, 27.

Flynn, M., et al., "Promoting Wound Healing: Wound Healing Mechanisms", American Journal of Nursing, Oct. 1992, pp. 1544-1558.

Hilton, P., "Surgical Wound Drainage: A Survey of Practices Among Gynaecologists in the British Isles", British Journal of Obstetrics and Gynaecology, Oct. 1988, pp. 1063-1069, vol. 95.

Milsom, I., et al., "An Evaluation of a Post-Operative Vacuum Drainage System", Current Medical Research and Opinion, 1979, pp. 160-164, vol. 6, No. 2.

Fox, J., et al., "The Use of Drains in Subcutaneous Surgical Procedures", The American Journal of Surgery, Nov. 1976, pp. 673-674, vol. 132.

Hulten, L., et al., "Primary Closure of Perineal Wound After Protocolectomy or Rectal Excision", Acta Chir Scand 137, 1971, pp. 467-469.

Landes, R., "An Improved Suction Device for Draining Wounds", Arch. Surg., May 1972, pp. 707, vol. 104.

Hugh, T., "Abdominal Wound Drainage", The Medical Journal of Australia, May 4, 1987, pp. 505.

Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265.

Bruno, P., "The Nature of Wound Healing", Nursing Clinics of North America, Dec. 1979, pp. 667-681, vol. 14, No. 4.

Bar-El, Y., et al., "Potentially Dangerous Negative Intrapleural Pressures Generated by Ordinary Pleural Drainage Systems", Chest, Feb. 2001, pp. 511-514, vol. 119, No. 2.

Agarwala, S., et al., "Use of Mini-Vacuum Drains in Small Surgical Wounds", Plastic and Reconstructive Surgery, Apr. 1998, pp. 1421-1422, vol. 101, n. 5.

Nasser, A., "The Use of the Mini-Flap Wound Suction Drain in Maxillofacial Surgery", Annals of the Royal College of Surgeons of England, 1986, pp. 151-153, vol. 68.

Lumley, J., et al., "The Physical and bacteriological Properties of Disposable and Non-Disposable Suction Drainage Units in the Laboratory", Br. J. Surg, 1974, pp. 832-837, vol. 61.

Britton, B., et al., "A Comparison Between Disposable and Non-disposable Suction Drainage Units: A Report of a Controlled Trial", Br. J. Surg, 1979, pp. 279-280, vol. 66.

Fay, M., "Drainage Systems: Their Role in Wound Healing", AORN Journal, Sep. 1987, pp. 442-451, vol. 46, No. 3.

Orgill, D., "Curent Concepts and Approaches to Wound Healing", Critical Care Medicine, Sep. 1988, pp. 899-908, vol. 16, No. 9.

"Making Sense of Wound Drainage", Nursing Times, Jul. 5, 1989, pp. 40-42, vol. 85, No. 27.

Harkiss, K., "Leg Ulcers Cheaper in the Long Run", Community Outlook, Aug. 1985, pp. 19, 21, 22, 24 & 26.

Westaby, S. (Editor), "Wound Care No. 43; Which Dressing and Why", Nursing Times Jul. 21, 1982, pp. 41-44.

Cobb, J., "Why Use Drains", The Journal of Bone and Joint Surgery, Nov. 1990, pp. 993-995, vol. 72-B, No. 6.

Garcia-Rinaldi, R., "Improving the Efficiency of Wound Drainage Catheters", the Journal of Surgery, Sep. 1975, pp. 372-373, vol. 130.

Silvis, R., et al., "The Use of Continuous Suction Negative Pressure Instead of Pressure Dressing", Annals of Surgery, Aug. 1955, pp. 252-256, vol. 1142, No. 2.

Van Way, C., "Prevention of Suction-Induced Gastric Mucosal Damage in Dogs", Gastric Suction, 1987, pp. 774-777, vol. 15, No. 8.

Curtin, L., "Wound Management: Care and Cost—An Overview", Nursing Management, Feb. 1984, pp. 22-25, vol. 15.

Royle, G., et al., "Disposable Drains", Annals of the Royal College of Surgery of England, 1984, 1 page, vol. 66.

Meehan, P., "Open Abdominal Wounds: A Creative Approach to a Challenging Problem", Pregressions, 1992, pp. 3-11, vol. 4, No. 2.

Stansby, G., et al., "Vacuum Drainage of Groin Wounds After Vascular Surgery", Br. J. Surg., Oct. 1990, pp. 1194-1195, vol. 77, No. 10.

Edlich, R., et al., "Evaluation of a New, Improved Surgical Drainage System", The American Journal of Surgery, Feb. 1985, pp. 295-298, vol. 149.

Broader, J., et al., "Management of the Pelvic Space After Proctectomy", Br. J. Surg., 1974, pp. 94-97, vol. 61.

Ayoub, M., et al., "A study of cutaneous and intracompartmental limb pressures associated with the combined use of tourniquets and plaster casts", May 1986, pp. 497, vol. 68-B, No. 3.

Cooper, D., "Optimizing Wound Healing: A Practice Within Nursing's Domain", Nursing Clinics of North America, Mar. 1990, pp. 165-179, vol. 25, No. 1.

Hollis, H., et al., "A Practical Approach to Wound Care in Patients With Complex Enterocutaneous Fistulas", Surgery, Gynecology & Obstetrics, Aug. 1985, pp. 179-181, vol. 161.

Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9.

Morykwas, M.J., et al., "Use of Negative Pressure to Increase the Rate of Granulation Tissue Formation in Chronic Open Wounds", The FASEB Journal, Apoptosis and Necrosis (799-800), Feb. 19, 1993.

Orringer, J.S., et al., "Management of Wounds in Patients with Complex Enterocutaneous Fistulas", Surgery, Gynecology & Obstetrics, Jul. 1987, vol. 165.

Swearingen, P.L., et al., "The Addison-Wesley Photo-Atlas of Nursing Procedures", 9 pages, © 1984.

Mulder, G.D, et al., Clinicians' Pocket Guide to Chronic Wound Repair, Wound Healing Publications Second Edition, 1992, pp. 1-107.

Peacock, E.E., Jr., Wound Repair:, Repair of Skin Wounds, 1984, pp. 172-175.

Jeter, Katherine F., et al., "Managing Draining Wounds and Fistulae: New and Established Methods", Chronic Wound Care, 1990, pp. 240-246.

Banwell, P, et al., "Topical Negative Pressure TNP Focus Group Meeting", Proceedings, London, UK 2003, 232 pages.

Proceedings from the 2003 National V.A.C.® Education Conference, supplement to the Apr. 2004 WOUNDS, 38 pages.

Dieu, T., et al., "Too Much Vacuum-Assisted Closure", ANZ J. Surg. 2003; 73: 1057-1060.

Chester, D., et al., "Adverse Alteration of Wound Flora with Topical Negative-Pressure Therapy: A Case Report", British Journal of Plastic Surgery, 2002, pp. 510-511.

Alvarez, A., et al., "Vacuum-Assisted Closure for Cutaneous Gastrointestinal Fistula Management", Gynecologic Oncology, 80, 413-416 (2001).

Nienhuijs, S.W., et al., "Can Topical Negative Pressure Be Used To Control Complex Enterocutaneous Fistulae?", Journal of Wound Care, V. 12, No. 9, Oct. 2003, pp. 343-345.

Maddin, W. Stuart, et al., "The Biological Effects of a Pulsed Electrostatic Field with Specific Reference to Hair", Pharmacology and Therapeutics, Jul. -Aug. 1990, V. 29, No. 6, pp. 446-450.

Peacock, Erle., Third Edition Would Repair, "Repair of Skin Wounds", W.B. Saunders Company 1984, 172-175.

Morykwas, M. and Argenta, L., "Use of Negative Pressure to Increase the Rate of Granulation Tissue Formation in Chronic Open Wounds", The FASEB Journal, Experimental Biology '93, New Orleans, Louisiana, Mar. 28-Apr. 1, 1993, 800.

Orringer, Jay, et al., "Management of Wounds in Patients with Complex Enterocutaneous Fistulas", Surgery, Gynecology & Obstetrics, Jul. 1987, V. 165, pp. 79-80.

Lohman, R., et al., "DISCUSSION: Vacuum Assisted Closure: Microdeformations of Wounds and Cell Proliferation", Plastic and Reconstructive Surgery, Oct. 2004, pp. 1097-1098.

Defranzo, A.J., et al., "109: Use of Sub-Atmospheric Pressure for Treatment of Gunshot Injuries", Plastic Surgical Forum, V. XXIII, Los Angeles, CA, Oct. 14-18, 2000, pp. 180-181.

Marks, M., et al., "Management of Complex Soft Tissue Defects in Pediatric Patients Using the V.A.C. Wound Closure", Plastic Surgical Forum, V. XXI, Boston, MA, Oct. 3-7, 1998, pp. 215-216.

Morykwas, M. and Argenta, L., "Use of Negative Pressure to Prevent Progression of Partial Thickness Burns", American Burn Association, V. 26, 26th Annual Meeting, Apr. 20-23, 1994, Orlando, Flordia, pp. 157.

Morykwas, M. and Argenta, L., "Vacuum Assisted Closure (VAC Therapy) for Secondary Closure of Dehisced and Infected Wounds", Wound Repair and Regeneration, Jul.-Sep. 1995, pp. 361.

Morykwas, M. and Argenta, L., "Treatment of Burned Extremities Using Vacuum Therapy (The V.A.C.)", Wound Repair and Regeneration, V. 3, N. 3, Jul.-Sep. 1995, pp. 367.

Webb, L. and Morykwas, M., et al., "The Use of Vacuum-Assisted Closure in Compsite Wound Management", The Third Riva Congress, Current Perspectives in Fracture Management and Orthopaedic Reconstruction, May 10-14, 2000, Italy, pp. 137.

Morykwas, M. and Webb, L., "Sub-Atmospheric Pressure for the Treatment of Lower Extremity Wounds", The Third Riva Congress, Current Perspectives in Fracture Management and Orthopaedic Reconstruction, May 10-14, 2000, Italy, pp. 135-136.

Argenta, L., et al., "Use of V.A.C. for Treatment of Dehisced Sternal Incisions", Plastic Surgical Forum, V. XXIII, Los Angeles, CA, Oct. 14-18, 2000, pp. 172-174.

Morykwas, M., et al., "Isolated Muscle Flap Survival with Complete Venous Occlusion: Varying Delay in External Application of Sub-atmospheric Pressure", Plastic Surgical Forum, V. XXI, Boston, MA, Oct. 3-7, 1998, pp. 237.

Morykwas, M., et al., "Vacuum-Assisted Closure: A New Method for Wound Control and Treatment: Animal Studies and Basic Foundation", Annals of Plastic Surgery, V. 39, N. 6, Jun. 1997, pp. 553-562.

Argenta, L. and Morykwas, M., "Vacuum-Assisted Closure: A New Method for Wound Control and Treatment: Clinical Experience", Annals of Plastic Surgery, V. 38, N. 6, Jun. 1997, pp. 563-576.

Morykwas, M. and Argenta, L., "V.A.C. Experience and Difficult Wounds", des Journees Regionales des Plaies et Cicatrisations, Sep. 22-23, 1997, pp. 76-90.

Genecov, D., et al., "A Controlled Subatmospheric Pressure Dressing Increases the Rate of Skin Graft Donor Site Reepithelialization", Annals of Plastic Surgery, V. 40, N. 3, Mar. 1998, 219-225.

Morykwas, M. and Argenta, L., "Techniques in Use of V.A.C.™ Treatment", ACA-Acta Chir. Austriaca, Supplement Nr. 150, 1998, pp. 3-4.

Morykwas, M. and Argenta, L., "Use of the V.A.C.™ For Treatment of a Traumatic Left Hip Disarticulation", ACA-Acta Chir. Austriaca, Supplement Nr. 150, 1998, pp. 24-25.

Morykwas, M., et al., "Use of Subatmosperic Pressure to Prevent Progression of Partialp Thickness Burns in a Swine Model", Journal of Burn Care & Rehabilitation, Jan./Feb. 1999, pp. 15-21.

Banwell, P., et al., "Application of Topical Sub-Atmospheric Pressure Modulates Inflammatory Cell Extravasation in Experimental Partial Thickness Burns", Wound Repair and Regeneration, Jul./ Aug. 1999, V. 7, N. 4, pp. A286-287.

Morykwas, M., et al., "Use of Subatomospheric Pressure to Prevent Doxorubicin Extravasation Ulcers in a Swine Model", Journal of Surgical Oncology, 1999; 72:14-17.

Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation.

Mooney, J., et al., "Treatment of Soft Tissue Defects in Pediatric Patients Using the V.A.C.™ System", Clinical Orthopaedics and Related Research, No. 376, Jul. 2000, pp. 26-31.

Morykwas, M., et al., "The Effect of Externally Applied Subatmospheric Pressure on Serum Myoglobin Levels After a Prolonged Crused/Ischemia Injury", The Journal of TRAUMA Injury, Infection and Critical Care, Sep. 2002, V. 53, N.3, pp. 537-540.

Molnar, J., et al., "Acceleration of Integra Incorporation in Complex Tissue Defects with Subatmospheric Pressure", Plastic and Reconstructive Surgery, Apr. 15, 2004, pp. 1339-1346.

Morykwas, M. and Argenta, L., "Nonsurgical Modalities to Enhance Healing and Care of Soft Tissue Wounds", Journal of the Southern Orthopaedic Association, V. 6, N. 4, 1997, pp. 279-288.

Schneider, A., et al., "A New and Reliable Method of Securing Skin Grafts to the Difficult Recipient Bed", Plastic and Reconstructive Surgery, Sep. 1998, pp. 1195-1198.

Rosser, C., et al., "A New Technique to Manage Perineal Wounds", Infections in Urology, Mar./Apr. 2000, V. 13, N.2, pp. 45-47 & 56.

Defranzo, A.J., et al., "The Use of Vacuum-Assisted Closure Therapy for the Treatment of Lower-Extremity Wounds with Exposed Bone", Plastic and Reconstructive Surgery, Oct. 2001, V. 108, N. 5, pp. 1184-1191.

Morykwas, M., "The Use of The V.A.C. Wound Treatment System for Acute and Subacute Wounds", Plaies & Cicatrices, Would Closure Healing, Apr. 21, 22 and 23, 1999.

Webb, L., et al., "Negative Pressure Wound Therapy in the Management of Orthopedic Wounds", Ostomy Wound Management, Apr. 2004, V. 50, Issue 4A (Suppl), pp. 26-27.

Webb, L., et al., "Wound Management With Vacuum Therapy", English abstract from website printout and German article, http://www.ncbi.nlm.nih.gov/entrez/query.fcgi?cmd=Retrieve&db=pubmed&dot=Abstra . . . , Dec. 2, 2004, 2 pages website printout, German article, Oct. 2001, pp. 918-926.

Webb, "New Techniques in Wound Management: Vacuum-Assisted Wound Closure", Journal of the American Academy of Orthopaedic Surgeons, V. 10, N. 5, Sep./Oct. 2002, pp. 303-311.

Morykwas, M. and Argenta, L., "Sub-Atmospheric Pressure Wound Treatment and Cultured Keratinocyte Allografts", Cultured Human Keratinocytes and Tissue Engineered Skin Substitutes, © 2001 Geor Thieme Verlag, pp. 343-346.

Molnar, J., et al., "Single-Stage Approach to Skin Grafting the Exposed Skull", Plastic and Reconstructive Surgery, Jan. 2000, V. 105, N. 1, 174-177.

Scherer, L., et al., "The Vacuum Assisted Closure Device: A Method of Securing Skin Grafts and Improving Graft Surival", Arch. Surg., V. 137, Aug. 2002, pp. 930-934.

Defranzo, A., et al., "Vacuum-Assisted Closure for the Treatment of Degloving Injuries", Plastic and Reconstructive Surgery, Dec. 1999, V. 104, N. 7, pp. 2145-2148.

Miller, P., et al., "Late Fascial Closure in Lieu of Ventral Hernia: The Next Step in Open Abdomen Management", the Journal of TRAUMA Injury, Infection and Critical Care, Nov. 2002, V. 53, N. 5, pp. 843-849.

Betancourt, S., "A Method of Collecting the Effluent From Complicated Fistula of the Small Intestine", 1986, p. 375.

Dorland's Illustrated Medical Dictionary, Twenty-Fifth Edition, 1974, pp. 1112.

Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682.

Montgomery, B., "Easy Dressing of Large, Draining Abdominal Wounds Using Moisture Vapor-Permeable Film", pp. 417-418, Techniques for Surgeons, Wiley Medical Publication, © 1985.

Davydov, Y., et al., "Pathogenic Mechanism of the Effect of Vacuum Therapy on the Course of the Wound Process", Jun. 1990, 15 pages of English Translation.

Borzov, M., et al., "Vacuum Therapy of Some Skin Diseases", Vestnik dermatologii venerologii, n. 8, Aug. 1965, pp. 50-56,(10 pages English translation by R. McElroy.

Herrmann, L., et al., "The Pavaex (Passive Vascular Exercise) Treatment of Obliterative Arterial Diseases of the Extremeties", The Journal of Medicine, Dec. 1933, pp. 524-529.

Herrmann, L., et al., "Passive Vascular Exercises: Treatment of Peripheral Obliterative Aterial Diseases by Rhythmic Alernation of Environmental Pressure", Archives of Surgery, v. 29, n. 5, Nov. 1934, pp. 697-704.

Sturr, R., Evaluation of Treatment of Peripheral Vascular Disease by Alternating Positive and Negative Pressure, Philadelphia, Archives of Physical Therapy, Sep. 1938, pp. 539-543.

Balin, A., et al., "Oxygen Modulates Growth of Human Cells at Physiologic Partial Pressure", Laboratory for Investigative Dermatology, J. Exp. Med. ©, the Rockefeller University Press, v. 160, Jul. 1984, pp. 152-166.

Saran Resins and Films, "Fresh Thinking". website printout, 6 pages, Jan. 20, 2004.

Bluesky Medical, "A Leader in Suction Technology—Wound Drainage Experts", printout of website, 55 pages, Apr. 8, 2003, www.blueskymedical.com.

Garcia-Rinaldi, R., et al., "Improving the Efficiency of Wound Drainage Catheters", v. 130,Sep. 1975, pp. 372-373.

Davydov, et al., "Would Healing Under the Conditions of Vacuum Draining", Khirurgiia (Mosk). 1992, (7-8): 21-6 (with English translation by Scientific Translation Services).

Davydov, et al., "Vacuum therapy in the treatment of acute suppurative diseases of soft tissue and suppurative wounds", Vestn. Khir, Sep. 1988 (with English translation by Ralph McElroy Co.).

Baker, B., "Negative-Pressure Therapy Looks Promising", Skin & Allergy News, Feb. 2000, p. 14.

McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-34.

Clinicians' Pocket Guide to Chronic Wound Repair, Wound Healing Publications, Seond Edition, © 1992, 106 pages.

Biblehimer, H., "Dealing with A Wound That Drains 1.5 Liters A Day", RN, Aug. 1986, pp. 21-22.

Barillo, D., et al., "Management of Burns to the Hand", Wounds 15,(1):4-9, 2003 Health Management Publications, Inc., Posted Feb. 12, 2003.

Medical Technology & Innovation, "Medical Technology is Extending Life, Reducing Costs", vol. 1, Issue 46, Dec. 4, 2000.

Chariker-Jeter Status Link from the website www.trademark.com/cbi-bin/tmlist, Oct. 14, 2005, 1 page.

Bluesky Medical Support, printout of webpages www.woundvacuum.com/Standard%20Pages/support.htm, Oct. 11, 2005, pp. 1-3.

Webster, J.G., "Prevention of Pressure Sores", © IOP Publishing Ltd 1991, The Adam Hilger Series on Biomedical Engineering, pp. 199-223.

Garcia-Velasco, M., et al., "Compression Treatment of Hypertrophic Scars in Burned Children", The Canadian Journal of Surgery, V.21, No. 5, Sep. 1978, pp. 450-452.

Rose, M.P., et al., "The Clinical Use Of A Tublar Compression Bandage, Tubigrip, for Burn-Scar Therapy: A Critical Anaylis", Burns (1985) 12, 58-64.

Spurlock, Gareth, "The Management of Open Joint Injuries", Wound Management, Veterinary Clinics of North American Equina Practice, vol. 5, No. 3, Dec. 1989.

Tittel, K., et al., "VariDyne—new standards in postoperative wound drainage", Jahrgang 14 (1988), Nr. 2, Apr. vol. 14 (1988), No. 2, Apr. pp. 104-107.

Queen, D., et al., "The preclinical evaluation of the Water Vapour Transmission Rate Through Burn Wound Dressings", Biomaterials 1987 vol. 8, Sep. , pp. 367-371.

Wood, R.A.B., et al., "Foam Elastomer Dressing in the Management of Open Granulating Wounds: Experience with 250 Patients", Br. J. Surg., vol. 64 (1977) , pp. 554-557.

Waymack, J.P., et al., "An Evaluation of Aquaphor Gauze Dressing in Burned Children", Burns (1986) 12, 443-448.

Winter, George D., "Epidermal Wound Healing Under a New Polyurethane Foam Dressing (Lyofoam)", Plastic & Reconstructive Surgery, Nov. 1975, Vo. 56, No. 5, pp. 531-537.

Thomas, S., et al., "Comparative Review of the Properties of Six Semipemeable Film Dressings", The Pharmaceutical Journal, Jun. 18, 1988, pp. 785-789.

Baker, B., "Abundance of Web Sites on Wound Care Management", Family Practice News, Mar. 1, 2000, pp. 52.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29.

WOUND TREATMENT EMPLOYING REDUCED PRESSURE

RELATED APPLICATIONS

This application is a continuation of co-pending application Ser. No. 09/026,353, entitled "Wound Treatment Employing Reduced Pressure," filed Feb. 19, 1998, which is a continuation of application Ser. No. 08/467,243, entitled "Wound Treatment Employing Reduced Pressure," filed on Jun. 6, 1995, abandoned, which is a continuation of application Ser. No. 08/028,677, entitled "Wound Treatment Employing Reduced Pressure," filed Mar. 9, 1993, now U.S. Pat. No. 5,636,643, issued Jun. 10, 1997, which is a continuation-in-part of application Ser. No. 07/792,001, entitled "Method of Treating Tissue Damage and Apparatus for Same," filed on Nov. 14, 1991, now U.S. Pat. No. 5,645,081, issued Jul. 8, 1997, such applications being incorporated herein by reference.

FIELD OF THE INVENTION

The present invention relates to an apparatus an method for treating a wound by applying reduced pressure to the wound.

BACKGROUND OF THE INVENTION

The treatment of open wounds that are too large to spontaneously close has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Poor blood circulation and infection at the wound may also hinder attachment of skin grafts or flaps upon wounded tissue. Skin grafts and flaps will not attach to tissue that is poorly vascularized, infected or necrotic. However, grafts and flaps can be used with much greater success on tissue that, although wounded, is able to form granulation tissue. Accordingly, a technique for promoting blood circulation at the wounded tissue would also promote successful attachment, or "take," of skin grafts or flaps to the wounded tissue as a consequence of increased blood circulation within the grafts or flaps.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise nonambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially cause the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

SUMMARY OF THE INVENTION

In accordance with the present invention a wound treatment apparatus is provided for treating a wound by applying reduced pressure (i.e. pressure that is below ambient atmospheric pressure) to the wound in a controlled manner for a selected time period. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

The wound treatment apparatus in accordance with the present invention includes a reduced pressure application appliance which is applied to a treatment site at which there is a wound and normal tissue surrounding the wound. The reduced pressure application appliance includes a fluid impermeable wound cover for covering and enclosing the wound. The appliance also includes sealing means for sealing the wound cover to the surrounding tissue of the wound in order to maintain reduced pressure in the vicinity in the wound during wound treatment. When the wound cover is sealed in position over the wound site, a generally fluid-tight or gas-tight sealed enclosure is formed over the wound site. The sealing means may be in the form of an adhesive applied to the underside of the wound cover for sealing the wound cover around the periphery of the wound. The sealing means may also include a separate sealing member such as an adhesive strip or a sealing ring in the form of a tubular pad or inflatable cuff secured to the wound cover for positioning around the periphery of the wound. In selected embodiments, the reduced pressure within the sealed enclosure under the wound cover may serve to seal the wound cover in position at the wound site. The reduced pressure appliance also includes a suction port for supplying reduced pressure within the sealed volume enclosed beneath the wound cover. The suction port may be in the from of a nipple on the wound cover. Alternatively, the suction port may be in the form of a tube attached to the wound cover or provided as a feedthrough beneath the wound cover. The appliance may also include a porous wound screen for placement in the wound or in position overlying the wound in order to prevent overgrowth of wound tissue during treatment. The wound screen is sufficiently porous to permit gas flow to the wound. The porous wound screen may be in the form of a sponge or open-cell foam material for placement in the wound. The porous screen may also include a rigid or semi-rigid screen for overlying the wound.

A vacuum system is connected with the reduced pressure appliance in order to provide suction or reduced pressure to the appliance. For this purpose, the vacuum system includes a suction pump or suction device for connection with the suction port of the appliance for producing the reduced pressure over the wound site. The vacuum system may include a section of hose or tube, such as a vacuum hose, that interconnects the suction device with the suction port of the appliance to provide the reduced pressure at the wound site. A collection device in the form of a fluid trap may be provided intermediate the vacuum hose of the suction device and the suction port of the appliance to trap any exudate which may be aspirated from the wound by the negative pressure appliance. A stop mechanism may also be provided for the vacuum system to halt production of the reduced pressure at the wound site in the event that an excessive quantity of exudate has been collected. The apparatus may also include a control device for controlling the pump and for providing intermittent or cyclic production of reduced pressure.

In a particular embodiment of the invention, the wound cover for the reduced pressure appliance may be in the form of a gas impermeable covering sheet of flexible polymer material, such as polyethylene, having an adhesive backing that provides the seal for securing the sheet over the wound site to provide an gas-tight or fluid-tight sealed enclosure over the wound site. The vacuum system of the wound treatment apparatus may include a suction pump having a vacuum hose that is connected with a suction tube serving as a suction port for the appliance. The suction tube for the appliance runs beneath the cover sheet that is sealed in position over the wound site and into the fluid-tight enclosure provided under the cover sheet. An adhesive backing on the cover sheet is used to provide a fluid-tight seal around the feedthrough for the suction tube at the wound site. Within the enclosure, the suction tube is connected with a piece of open-cell foam for placement in the wound. The open-cell foam functions to more uniformly apply reduced pressure or suction over the wound site while holding the cover sheet substantially out of the wound during the application of reduced pressure at the enclosed wound site.

In operation, a method of treating tissue damage is provided which comprises applying a negative or reduced pressure to a wound over an area sufficient to promote the migration of epithelial and subcutaneous tissue toward the wound and for a time period sufficient to facilitate closure of the wound. The method is useful for treating pressure sores.

A method of treating a burn wound is also provided which comprises applying a negative or reduced pressure to the burn over an area and for a time sufficient to inhibit progression in the depth of the burn. The method is useful on a partial thickness burn soon after its infliction.

A method of treating tissue damage is also provided which comprises applying a negative or reduced pressure to a wound for a time sufficient to reduce bacterial density in the wound. One use of this method is its application to a wound for a selected time period such as at least three days to reduce the bacterial density of an infected wound to the point at which surgical closure can be attempted.

Another aspect of the invention is a method of enhancing the attachment of adjacent tissue to a wound which comprises applying negative or reduced pressure to a joined complex of the adjacent living tissue and the wound at a sufficient magnitude of reduced pressure and for a sufficient time duration to promote the migration of epithelial and subcutaneous tissue toward the complex. This method enhances attachment of adjacent tissue to tissues of the wound edges. Another use of this method is to enhance attachment of an open skin graft to the wound tissue.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENTS

Figure 10:
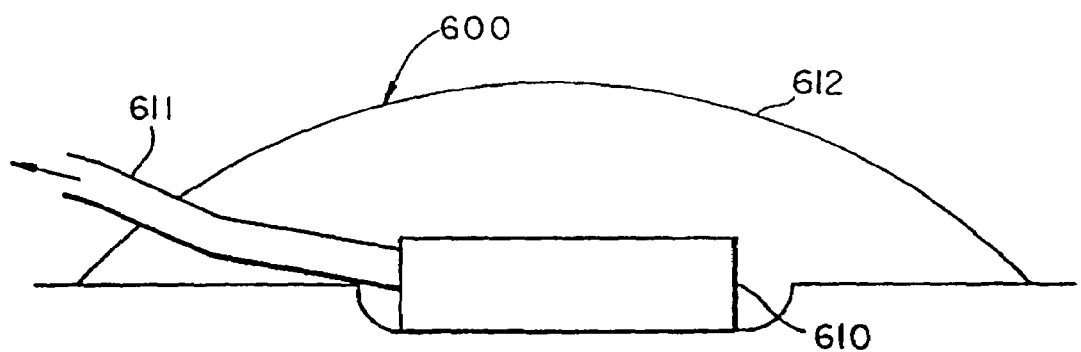
FIG. 10 is a schematic cross-sectional view of a reduced or negative pressure appliance comprising an open-cell polymer foam screen, a flexible hose for connecting the foam screen with a vacuum system, and an adhesive-backed flexible polymer sheet overlying the foam-hose assembly to provide a seal over a wound.

In accordance with the present invention, a wound treatment apparatus is provided for treating a wound by application of reduced pressure (i.e., below atmospheric pressure) so that suction may be applied to a wound site in a controlled manner for a selected time period. As schematically shown in FIG. 10, a wound treatment apparatus includes a reduced pressure appliance, generally designated 600, which is applied to a wound site to treat the wound through the application of reduced pressure. The appliance 600 is sealed in position over the wound site to create a generally fluid-tight or gas-tight enclosure over the wound site.

The appliance 600 includes a substantially flat section of open cell polyester foam section 610 (Fischer Scientific, Pittsburgh, Pa. 15219) sufficiently large to cover the wound and thus prevent wound overgrowth, a flexible hollow tube 611 (Fischer Scientific) inserted into the open cell foam section 610 and joined thereto with an adhesive and extending to attach at its opposite end with a Gast Vacuum pump (Fischer Scientific), and an Ioban adhesive sheet 612 (Minnesota Mining and Manufacturing, St. Paul, Minn. 55144) overlying the foam section 610 and tubing 611 and adhered to the skin surrounding the wound, thus forming a seal that allows creation of a vacuum when the suction pump operates. Such an appliance 600 would most preferably be packaged in a sterile condition to ameliorate the need for sterilization of the apparatus prior to use. The adhesive sheet 612 may be packaged separately from the foam-tube assembly 610 and 611. A particular advantage of this configuration is its use with pressure sores because the device can be placed in the depths of the wound and the patient can lie upon the device without either affecting the utility of the device or further damaging the wound. This becomes critical if the patient cannot be moved from this posture for medical or other reasons.

Figure 11:
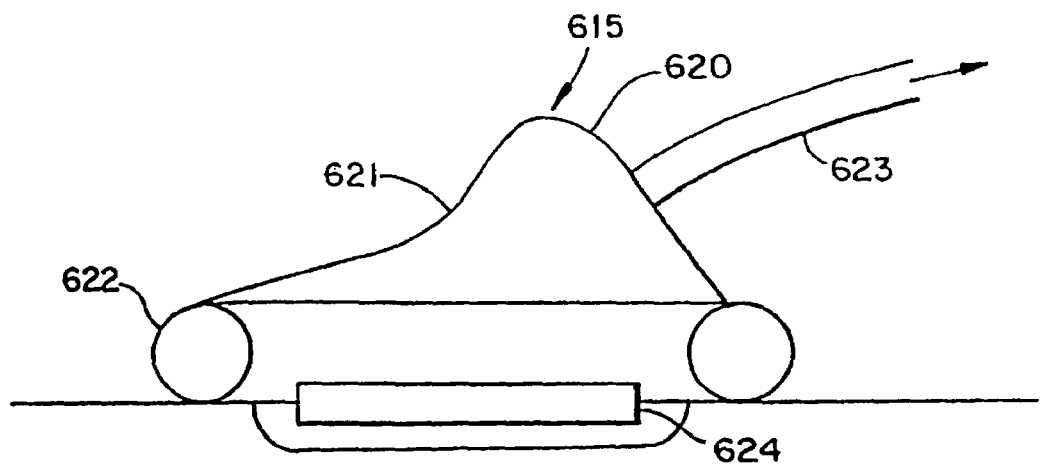
FIG. 11 is a schematic cross-sectional view of a reduced or negative pressure appliance comprising a rigid porous screen for a wound, a rigid or semi-rigid cup for covering the wound having an inflatable cuff attached about the base of the cup, and a flexible hose extending from the cup for connection with a vacuum system.

As shown in FIG. 11, a reduced pressure appliance, generally designated 615, in accordance with another embodiment of the present invention, is schematically depicted. The reduced pressure appliance 615 includes an adult CPR mask 620 (Doug Brown and Associates, Huntington Beach, Calif. 92648) comprising a rigid or semi-rigid fluid impermeable cup 621 having an inflatable cuff 622 mounted around the periphery of the base of the cup 622 for contact with the skin, an open cell polyester screen 624 overlying the wound, and a flexible ¼ inch diameter hose 623 (Fischer Scientific) connected by a Nalgene tubing connector extending through a sealed hole in the cup for connection with a vacuum pump (Fischer Scientific). The hose 623 is connected with the pump 40 of a vacuum system 30 of the type shown in FIG. 1 to provide reduced pressure within the cup 621. The vacuum created within the cup 621 by the vacuum system may be sufficient to seal the cup in position over the wound site. Alternatively, fluid impermeable adhesive covering or strips may also be used to seal the appliance 615 in proper position.

Figure 1:
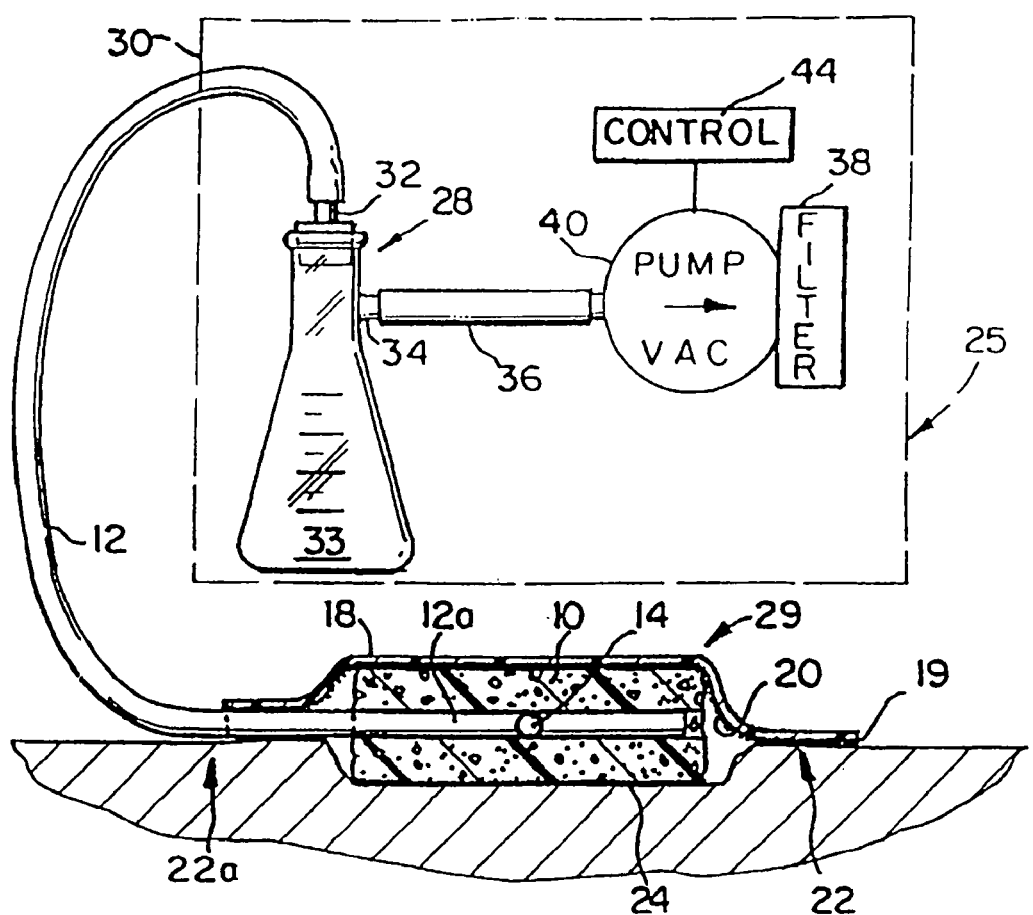
FIG. 1 is a schematic elevational view of a wound treatment apparatus in accordance with the present invention in which a reduced pressure appliance, shown in partial section, includes a flexible, fluid impermeable wound cover sealed over the wound and a foam wound screen positioned in the wound, and in which a vacuum system provides reduced pressure within the wound cover of the appliance.

Referring to FIG. 1, a wound treatment apparatus, generally designated 25, is depicted having a reduced pressure appliance 29 for enclosing a wound site to provide a fluid-tight or gas-tight enclosure over the wound site to effect treatment of a wound 24 with reduced or negative pressure. The wound treatment apparatus 25 includes a reduced pressure appliance, generally designated 29, which is applied to and sealed over a wound site in order to enclose the wound site for treatment with suction or reduced pressure within a sealed generally fluid-tight or gas-tight enclosure. For the purpose of creating suction within the appliance 29, the appliance 29 is connected with a vacuum system, generally designed 30, to provide a source of suction or reduced pressure for the sealed appliance 29 at the wound site. The appliance 29 includes a fluid-impermeable wound cover 18 in the form of a flexible, adhesive, fluid impermeable polymer sheet for covering and enclosing the wound 24 and the surrounding normal skin 22 at the wound site. The wound cover 18 includes an adhesive backing 20 which functions to seal the wound cover to the normal skin 22 around the periphery of wound 24 to provide a generally gas-tight or fluid-tight enclosure over the wound 24. The adhesive cover sheet 18 must have sufficient adhesion to form a fluid-tight or gas-tight seal 19 around the periphery of the wound and to hold the sheet 18 in sealed contact with the skin during the application of suction or reduced or negative pressure.

The appliance 29 also includes a porous wound screen 10 which is placed within the wound 24. The wound screen 10 is placed over substantially the expanse of the wound to prevent its overgrowth. The size and configuration of the wound screen 10 can be adjusted to fit the individual wound. It can be formed from a variety of porous materials. The material should be sufficiently porous to allow oxygen to reach the wound. The wound screen 610 may be in the form of an open-cell polymer foam, such as a polyurethane foam, which is sufficiently porous to allow gas flow to and/or from the wound 24. Foams may be used that vary in thickness and rigidity, although it may be desirable to use a spongy material for the patient's comfort if the patient must lie upon the appliance during treatment. The foam may also be perforated to enhance gas flow and to reduce the weight of the appliance. As shown in FIG. 1, the screen 10 is cut to an appropriate shape and size to fit within the wound 24. Alternatively, the screen may be sufficiently large to overlap the surrounding skin 22.

The appliance 29 also includes a suction port in the form of a hollow suction tube 12 that connects with the vacuum system 30 to provide suction within the sealed enclosure. The suction tubing 12 serves as a suction port for appliance 29. An end segment 12a of the tubing 12 is embedded within the foam screen 10 for providing suction or reduced pressure within the enclosure provided under the wound cover 18. Embedding the open end of segment 12a of tubing 12 within the interior of the foam screen 10 permits the foam screen 10 to function as a shield to help prevent the wound cover 18 from being inadvertently sucked into sealing engagement with the open end of the tube thereby plugging the tube 12 and restricting gas flow. The tube segment 12a embedded within the foam screen 10 preferably has at least one side port 14 for positioning within the interior of the foam screen 10 to promote substantially uniform application of reduced pressure throughout the enclosure. Positioning the side port 14 of tube segment 12a within the interior of the foam screen 10 permits the foam screen 10 to function as a shield for the side port to thereby prevent the wound cover 18 from being sucked into the side port 14 and thereby restricting gas flow. The open cells of the foam screen 10 facilitate gas flow throughout the enclosure. In addition, the foam screen 10 functions to prevent wound overgrowth and to hold the wound cover 18 generally out of contact with the wound 24 during the application of suction within the enclosure.

Tubing 12 and tube segment 12a are sufficiently flexible to permit movement of the tubing but are sufficiently rigid to resist constriction when reduced pressure is supplied to the appliance 29 or when the location of the wound is such that the patient must sit or lie upon the tubing 12 or upon the reduced pressure appliance 29. The screen-tube assembly comprising the foam screen 10 and the tube 12 may be fabricated by snaking the end of the tube segment 12a through an internal passageway in the foam screen 10 such as by pulling the end of the tube segment 12a through the passageway using forceps. Alternatively, fabrication of the screen-tube assembly may be accomplished by suspending the end of the tube segment 12a into a suitable mold or form and then blowing foam into the mold or form to embed the tube end segment 12a within the blow-molded foam screen. The screen-tube assembly 12 and 10 is preferably prepared prior to use under sterile conditions and then stored in an aseptic package.

In order to use the reduced pressure appliance 29 at the site of the wound 24, the flexible, gas-impermeable, adhesive wound cover sheet 18 is secured in position at the wound site overlying the foam screen 10 disposed within the wound 24. The wound cover sheet 18 is secured and sealed to the surrounding normal skin 22 by an adhesive layer 20 on the under surface of the wound cover 18 to form a gas-tight seal 19 around the periphery of the wound 24. The wound cover 18 also provides a gas-tight seal around the tubing 12 at the feedthrough location 22a where the tubing 12 emerges from beneath the wound cover 18. The wound cover 18 is preferably formed of a fluid impermeable or gas impermeable flexible adhesive sheet such as Ioban, a product of the 3M corporation of Minneapolis, Minn.

The vacuum system 30 includes a suction pump 40 that produces a source of reduced pressure or suction which is supplied to the reduced pressure appliance 29 by suction tubing 12. As shown in FIG. 1, a fluid trap, generally designated 28, is interconnected between the suction pump 40 and the appliance 29 to remove and collect any exudate which may be aspirated from the wound 24 by the reduced pressure appliance. The appliance 29 functions to actively draw fluid or exudate from the wound 24. Collection of exudate in a fluid trap 28 intermediate the pump 40 and the appliance 29 is desirable to prevent clogging of the pump 40. A suitable fluid trap 28 may be assembled from an Erlenmeyer or side-arm flask 31 having a top opening and a side-arm opening. The fluid trap 28 includes a first port 32 at the top opening of the flask for sealed connection to suction tubing 12. The first port 32 enables suction to be applied to the reduced pressure appliance 29 through the tubing 12 and also enables exudate from the wound covered by reduced pressure appliance 29 to be drained into the flask 31. The flask 31 provides a collecting vessel 33 for the fluid trap for containing and temporarily storing the collected exudate. A suction port 34 is provided at the side-arm opening of the flask to enable the application of suction from vacuum pump 40. The suction port 34 of the fluid trap 28 is connected to the vacuum pump 40 by vacuum line 36. The fluid trap 28 is sealed generally gas-tight to enable the suction pump 40 to supply suction to the appliance 29 through the fluid trap 28. A filter 38 such as micropore filter is preferably attached to the exhaust of the pump 40 to prevent potentially pathogenic microbes or aerosols from being vented to atmosphere by the vacuum pump 40.

Predetermined amounts of suction or reduced pressure are produced by the vacuum pump 40. The vacuum pump 40 is preferably controlled by a control device 44 such as a switch or a timer which may be set to provide cyclic on/off operation of the vacuum pump 40 according to user-selected intervals. Alternatively, the vacuum pump 40 may be operated continuously without the use of a cyclical timer.

The vacuum system 30 preferably includes a shut-off mechanism for halting or inhibiting the supply of the reduced pressure to the appliance 29 in the event that the exudate aspirated from the wound 24 exceeds a predetermined quantity. Interrupting the application of suction to the appliance 29 is desirable to prevent exsanguination in the unlikely event a blood vessel ruptures under the wound cover 18 during treatment. If, for example, a blood vessel ruptures in the vicinity of the wound 24, a shut-off mechanism would be useful to prevent the vacuum system 30 from aspirating any significant quantity of blood from the patient. As a safety feature, various mechanical or electrical detection mechanisms may be employed to detect the level of exudate in the fluid trap 28.

Figure 7:
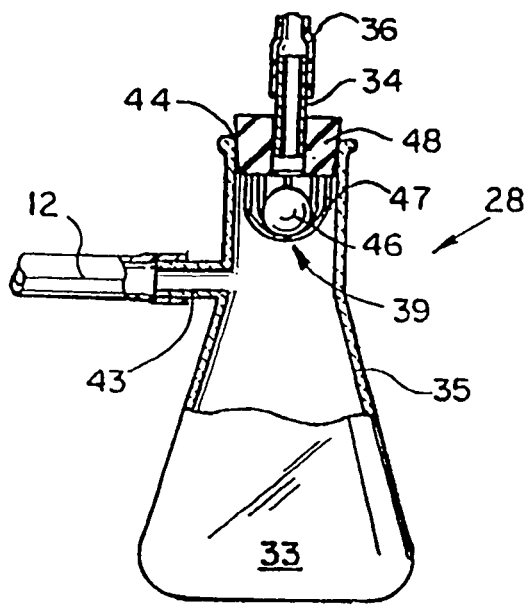
FIG. 7 is a schematic elevational view in partial section of an alternative fluid collection device having a float valve for use in the vacuum system of FIG. 1.

As shown in FIG. 7, a fluid trap 28 employing a collection bottle or flask 35 is provided for connection intermediate the pump 40 and the appliance 29 for collecting exudate from the wound site. The flask 35 has a side-arm port 43 connected to suction tube 12 leading to the reduced pressure appliance 29 and a suction port 34 located at the top 44 of the flask 35 connected to the vacuum hose 36 leading to the vacuum pump 40. For the purpose of detecting liquid level within the flask 35, a float valve assembly, generally designated 39, is provided. The float-valve assembly 39 functions to close and seal off the suction port 34 of the fluid trap 28 when the quantity of exudate in the collecting vessel 33 exceeds a predetermined quantity. The float valve assembly 39 is provided in the form of a ball 46 which is held and suspended within a cage 47 positioned below a valve seat 48 disposed within the opening at the top 44 of the flask 35. The ball 46 has a specific gravity below that of the exudate so that the ball 46 will float upon the exudate and will be lifted against the valve seat 48 as the vessel 33 fills with exudate. When the ball 46 is firmly seated against the valve seat 48, the float valve 39 blocks suction port 34 and thereby shuts off the source of suction from vacuum line 36. The suction within the appliance 29 at the wound site arrests thus halting the aspiration of exudate from the wound.

Figure 8:
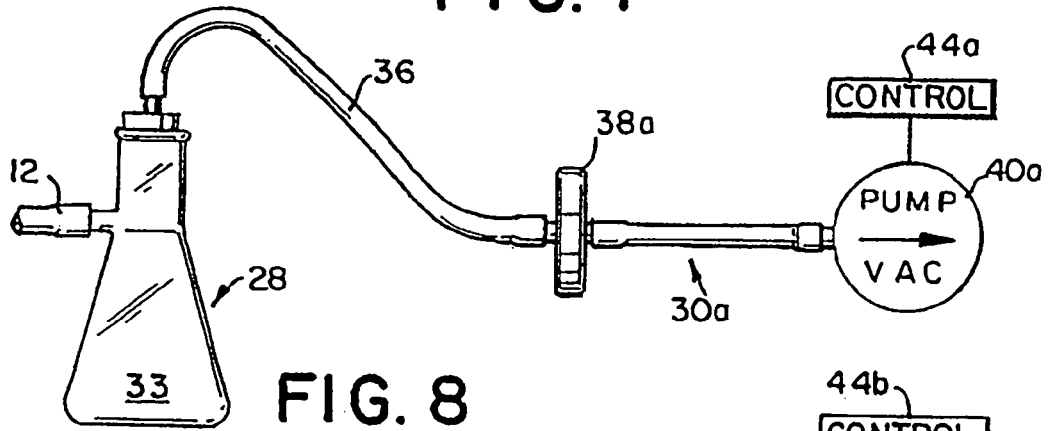
FIG. 8 is a schematic view of an alternative vacuum system.

Other types of mechanisms may be employed to detect the liquid level within the fluid trap 28 in order to arrest operation of the vacuum source. An alternative vacuum system 30a is shown in FIG. 8 in which a filter 38a is employed in vacuum line 36 for filtering the fluid or gas flow through the vacuum line 36 and for detecting the level of liquid in fluid trap 28. Exudate from the wound is collected in vessel 33. When the vessel 33 becomes full, aspiration of further exudate from the wound causes the vacuum line 36 to begin to collect exudate which eventually reaches the in-line filter 38a positioned in the vacuum line 36 intermediate the fluid trap 28 and the pump 40a having operational control 44a. The filter 38a contains a filter element that is selected to clog when exposed to sufficient amounts of moisture to thereby halt the supply of suction through the fluid trap 28 to the appliance 29. The filter 38a is preferably an in-line, disc-shaped submicron filter having a nitrocellulose or PTFE filtration element for filtering particles larger than about 0.1 μm from the vacuum line 36. In addition to preventing excess fluid aspiration, the filter 38a in the vacuum line 36 prevents contamination of the vacuum pump 40 by filtering potentially pathogenic microbes and aerosols.

Figure 9:
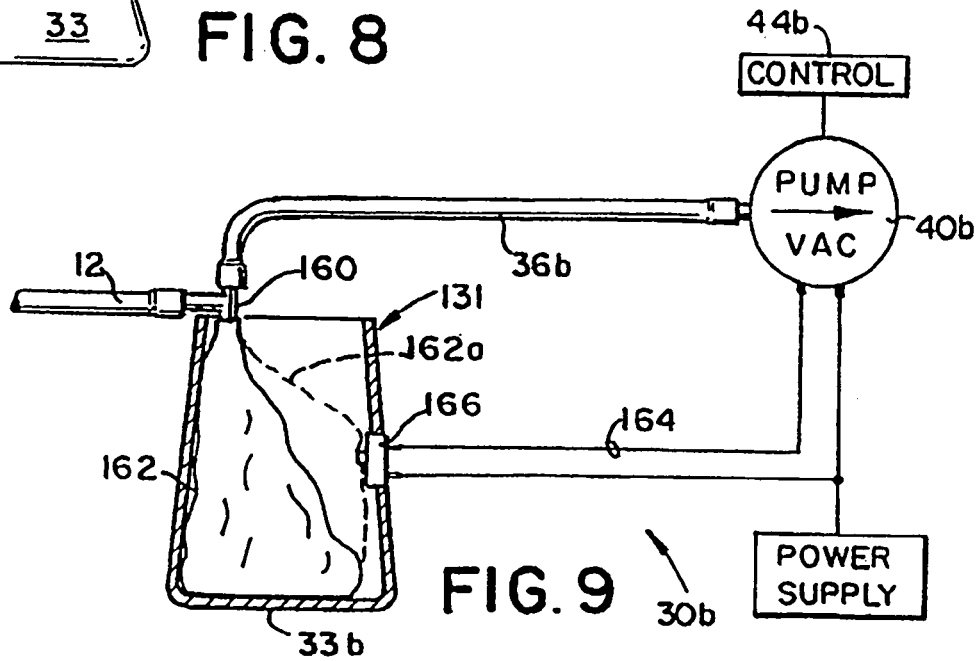
FIG. 9 is a schematic view of an alternative vacuum system incorporating a fluid collection device having an actuator for de-activating the vacuum system upon collection of a predetermined quantity of fluid.

Other types of detection devices may also be employed to detect a predetermined level of liquid collected in collection vessel 33. For example, collection of exudate in excess of a predetermined quantity may enable actuation of an electronic switch which turns off the vacuum pump or otherwise halts the supply of suction to the reduced pressure appliance 29. Referring to FIG. 9, the suction tubing 12 from the reduced pressure appliance 29 is connected to a three-port coupling device 160 that interconnects suction tube 12, vacuum line 36b and fluid collecting apparatus 131. The coupling device 160 permits transmission of suction from the vacuum line 36b of the pump 40b to the suction tubing 12. The coupling device 160 also permits aspirated exudate from tubing 12 to be collected in an expandable container, such as an intravenous fluid bag 162, housed beneath the coupling device 160 in a rigid housing vessel 33b. As exudate is collected, the bag 162 expands to conform to the shape of the interior surface of the surrounding rigid vessel 33b. An actuator 166, such as a spring-loaded actuator switch, is located within the side wall of the rigid vessel 33b and functions to shut off the pump 40b upon actuation of the switch 166. When the bag 162 expands sufficiently to contact and actuate switch 166 as shown in dashed lines at 162a in FIG. 9, the switch 166 is opened and the supply of power to the pump 40b along power line 164 is interrupted and the supply of suction to the appliance 29 is stopped. The actuator switch 166 may also cooperate with control 44b for the pump 40b to stop operation of the pump 40b. Other types of devices may also be employed to detect fluid levels in fluid trap 28. For example, weight detectors may be employed to detect a predetermined weight limit as the fluid trap fills with exudate or other liquid. Alternatively, optical sensors or detectors may also be employed.

Figure 2:
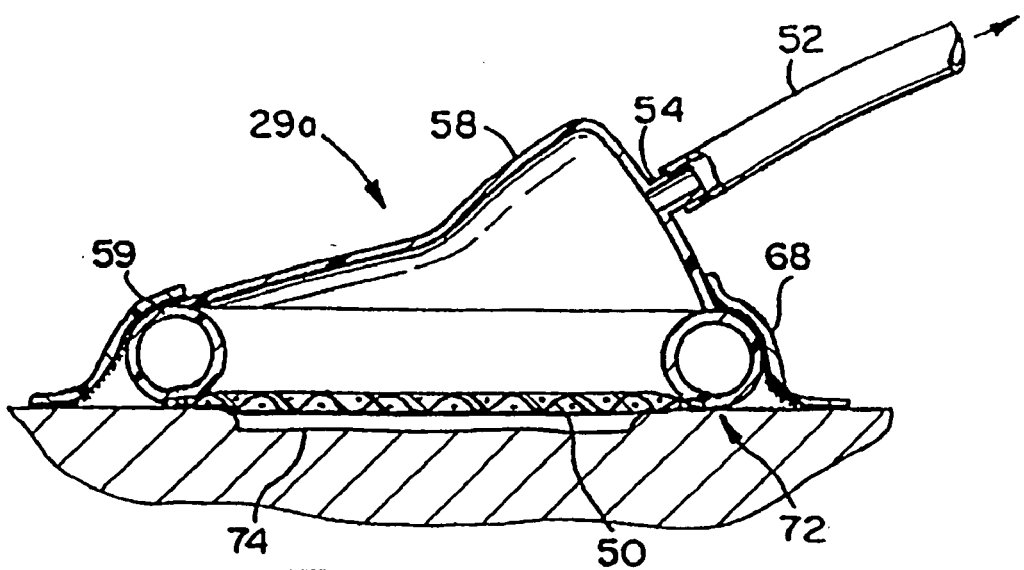
FIG. 2 is a schematic sectional elevational view of a reduced pressure appliance in accordance with another embodiment of the present invention having a rigid, fluid impermeable wound cover sealed over a wound and a rigid or semi-rigid screen overlying the wound.

For the purpose of protecting the site of a wound from impact or abrasion during treatment, a reduced pressure appliance employing a rigid or semi-rigid wound cover may be utilized over the site of the wound. As shown in FIG. 2, a reduced pressure appliance 29a includes a CPR mask 58 that provides a rigid wound cover for enclosing an appropriately-sized wound 74. The mask 59 is impermeable to fluids or gases so that a fluid-tight or gas-tight enclosure is effected over the wound site. The mask 59 is sufficiently rigid to support itself away from the wound during the application of suction or reduced pressure so that the mask 59 does not collapse into the wound 74. The CPR mask 58 is of the type having an inflatable air cuff 59 around the base of the mask. The cuff 59 may be inflated via an external valve for sealing the mask 59 against the normal skin 72 around the periphery of the wound 74. The air cuff 59 also prevents the base of the mask from digging into the skin 72 during application of reduced pressure. An optional screen 50 for preventing overgrowth of the wound 74 may be positioned to overlie the wound 74. The screen 50 may be formed of a rigid or semi-rigid perforated polymer surgical mesh such as Prolene mesh. Alternatively, a section of honeycombed polyethylene sheet may be cut to a suitable size and shape to overlie the wound 74. The screen 50 is held against the surrounding normal skin 72 in position overlying wound 74 by the cuff 59 which overlaps at least a portion of the periphery of the screen 50. The CPR mask 58 also includes a suction port in the form of a hose connector 54 to which one end of a suction tube 52 is attached. The other end of tube 52 is connected with a vacuum system 30 of the type previously described to provide a source of suction or reduced pressure for the appliance 29a. Suction produced within the appliance 29a may be sufficient to seal the cuff 59 to the skin and to thereby seal the appliance 29a in position over the wound site. However, in order to ensure a gas-tight seal between the reduced pressure appliance 29a and the surrounding skin 72, the mask 58 may also be secured to the treatment site with a fluid impermeable adhesive seal 68. The adhesive seal 68 may be formed of a flexible adhesive material such as an adhesive tape or an adhesive sheet that has been cut to surround and at least partially overlie the cuff 59. As shown in FIG. 2, the adhesive seal is secured to the base portion of the rigid mask 58 and to the normal skin 72 around the periphery of the air cuff 59 to seal the mask in position over the wound site.

Figure 3:
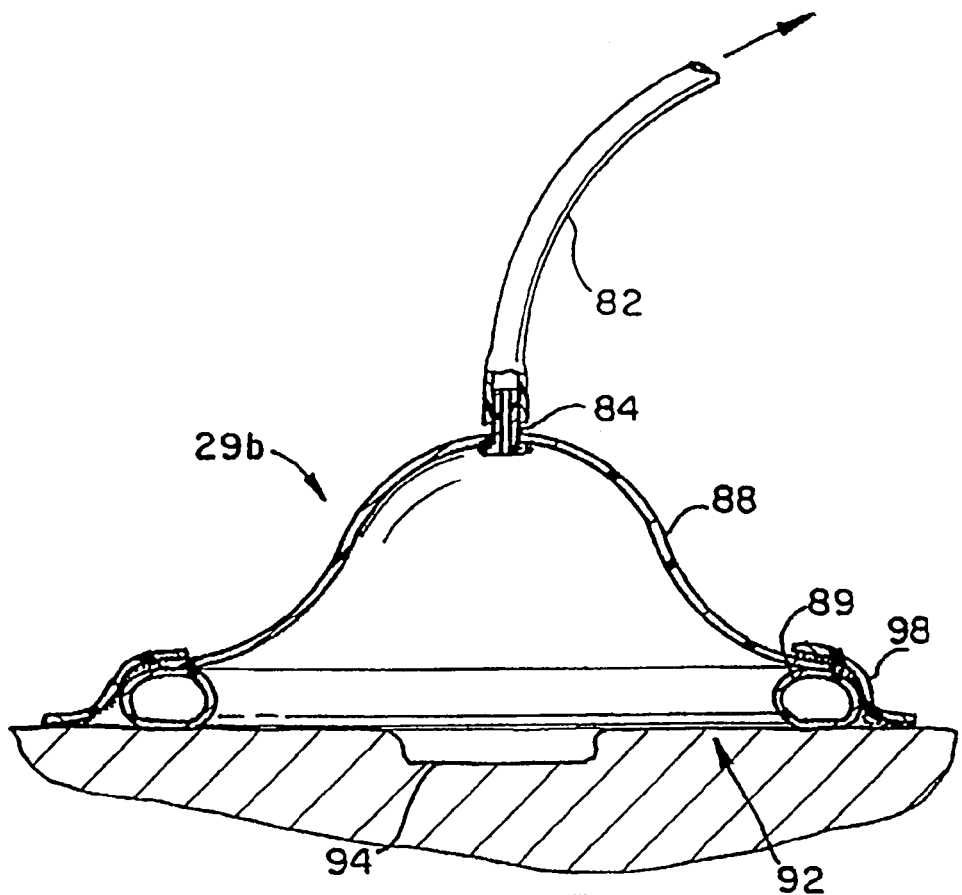
FIG. 3 is a schematic sectional elevational view of a reduced pressure appliance in accordance with another embodiment of the present invention having a rigid, fluid impermeable wound cover sealed over a wound.

As shown in FIG. 3, a reduced pressure appliance 29b is depicted having a rigid, fluid impermeable, cup-shaped wound cover 88 overlying a wound site. The appliance 29b is used to treat a wound 114 without any screen either in the wound or overlying the wound. The cover cup 88 can be formed of a polymer such as polystyrene, HDPE, or other suitably rigid material. The cup 88 must be sufficiently rigid to support itself out of contact with the wound 114 during the application of suction or negative pressure so that the cup 88 does not collapse into the wound. Reduced pressure is supplied to the interior of the cup 88 through the suction tubing 82 connected to suction port 84 in the form of a nipple sealed in position on the cup 88. The tubing 82 is also connected with a suitable vacuum system 30 of the type previously described to provide a source of suction or negative pressure within the appliance 29b. The base of the cup 88 supports an inflatable air cuff 89 to seal the cup 88 to the skin and to prevent the cup 88 from digging into the skin 92 and causing discomfort when reduced pressure is applied. The cuff 89 is positioned upon the normal skin 92 surrounding the wound 94. While the suction created within the cup 88 may be sufficient to hold the appliance in position by causing the air cuff to seal to the skin, more effective attachment of the appliance to the surrounding skin 92 may be obtained by the use of a strip of fluid impermeable, adhesive material secured to the skin 102 and to the base of the cup 88 over the air cuff 89 around the periphery of the base of the cup 88. The layer of adhesive material 98 helps to ensure that a fluid-tight or gas-tight seal is maintained between the cup 88 and the surrounding skin 92 so that a fluid-tight enclosure is formed over the wound site.

Figure 4:
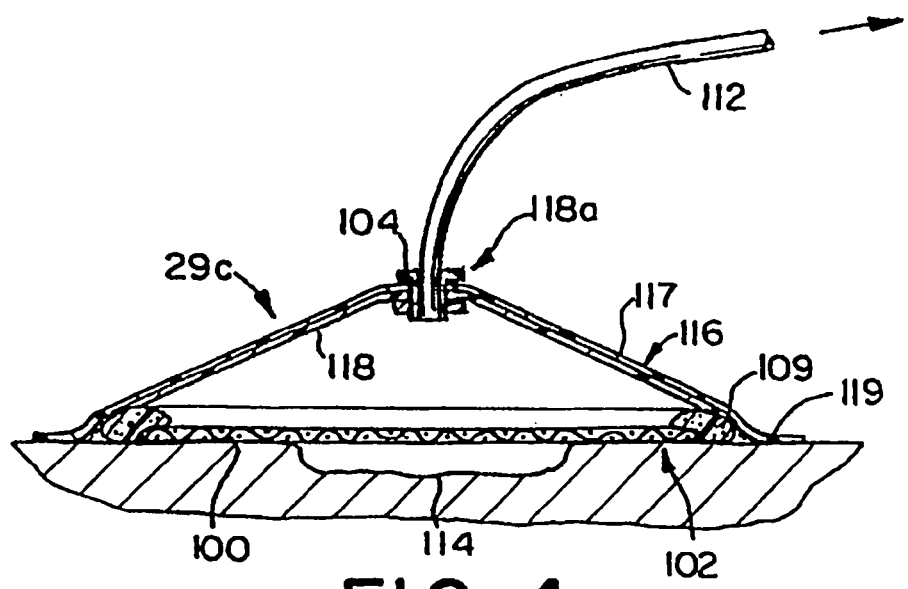
FIG. 4 is a schematic sectional elevational view of a reduced pressure appliance in accordance with another embodiment of the present invention having a semi-rigid, fluid impermeable cover enclosing a wound and a rigid or semi-rigid screen overlying the wound, with an overlying flexible fluid impermeable cover sheet sealing the enclosure over the wound.

Referring to FIG. 4, a reduced pressure appliance 29c is depicted for enclosing a wound site for the treatment of wound 114 with suction or reduced pressure. The reduced pressure appliance 29c includes a fluid-impermeable wound covering, generally designated 116, having an outer flexible, adhesive polymer sheet 117 applied over an inner, generally circular, semi-rigid shield 118, such as a polystyrene shield, for covering and enclosing the wound site. The base of the shield 118 is positioned over a circular pad 109 which may be formed from flexible tubing to prevent the base of the cup from digging into the skin 102 and causing discomfort when suction is applied to the appliance 29c. The pad 109 may also facilitate sealing of the cover shield 118 in position over the wound site to form a fluid-tight or gas-tight enclosure over the wound site. The pad 109 may be positioned directly onto the normal skin 102 surrounding the wound 114 or, as shown in FIG. 4, the pad 109 may overlie an outer peripheral portion of a rigid screen 100 in order to hold the screen 100 in a position overlying the wound to prevent wound overgrowth. A suction port 104 is provided at the top of the shield 118 to permit gas-tight connection to suction tube 112. The suction port 104 may be in the form of a removable connector that is screwed into position at the top of the shield 118. Suction tube 112 functions to connect the appliance 29c to a suitable vacuum system 30 of the type previously described. For the purpose of enhancing the sealing of the appliance 29c in position over the wound site, an over-sized, generally circular, adhesive, fluid impermeable polymer sheet 117 is adhered and secured to the top surface of the shield 118. The oversized adhesive sheet 117 extends beyond the outer periphery of the shield 118 so that the adhesive sheet 117 provides a sealing ring 119 of material around the periphery of the shield. The sealing ring 119 is sealed and adhered to the normal skin 102 around the outer periphery of pad 109. When sealed in position overlying wound 114, the appliance 29c provides a generally fluid-tight or gas-tight enclosure over the wound site.

Figure 5:
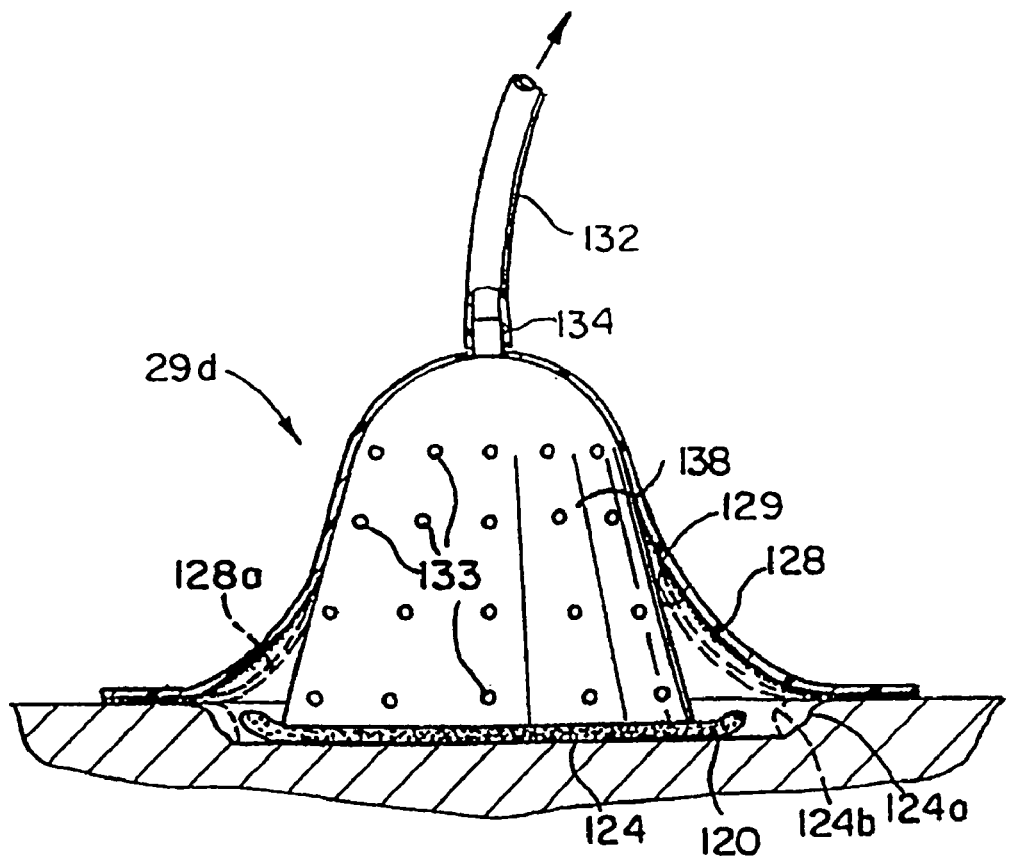
FIG. 5 is a schematic elevational view of a reduced pressure appliance, shown in partial section, in accordance with another embodiment of the present invention having a flexible, fluid impermeable wound cover over an inner rigid porous support cup.

Referring to FIG. 5, a reduced pressure appliance 29d is depicted for enclosing and treating a wound 124 with suction or reduced pressure. A rigid or semirigid porous cup 138 is placed rim side down upon a porous screen or pad 120 located within a wound 124. The cup 138 has perforations 133 for equalizing pressure inside and outside of the cup 138. A flexible, fluid impermeable adhesive polymer cover sheet 128 is draped over the cup 138 to enclose the wound 124. The adhesive cover sheet 128 is adhered and sealed to the top portion of the cup 138 and to the surrounding normal skin 122 by adhesive layer 129 on the underside of the cover sheet 128 to provide a fluid-tight enclosure beneath the sheet 128. The cup 138 provides a generally central support beneath the cover sheet 128 to hold the cover sheet 128 out of contact with the wound 124 during application of suction. The cup 138 has a central suction port 134 sealed in position at the top of the cup 128 to permit connection by suction tube 132 to a vacuum system 30 of the type previously described. When reduced pressure is supplied to the appliance 29d, the cover sheet 128 is deformed downward and inward to position 128a as shown in phantom in FIG. 5. Tension developed within the deformed sheet 128a by virtue of the suction is exerted upon the surrounding skin by the sheet at position 128a. The outer periphery 124a of the wound 124 is pulled inward by virtue of such tension to the position shown in phantom at 124b to promote closure of the wound. The tension within the sheet at position 128a also exerts a downward force upon the cup 138 which more firmly presses the cup 138 onto the wound 124. Such downward force on the cup 138 may be desired in such applications as flap or graft attachment to promote contact between the flap or graft and the underlying tissue. The pad 124 under the cup 138 helps to alleviate discomfort caused by the downward force on the cup 138.

Figure 6:
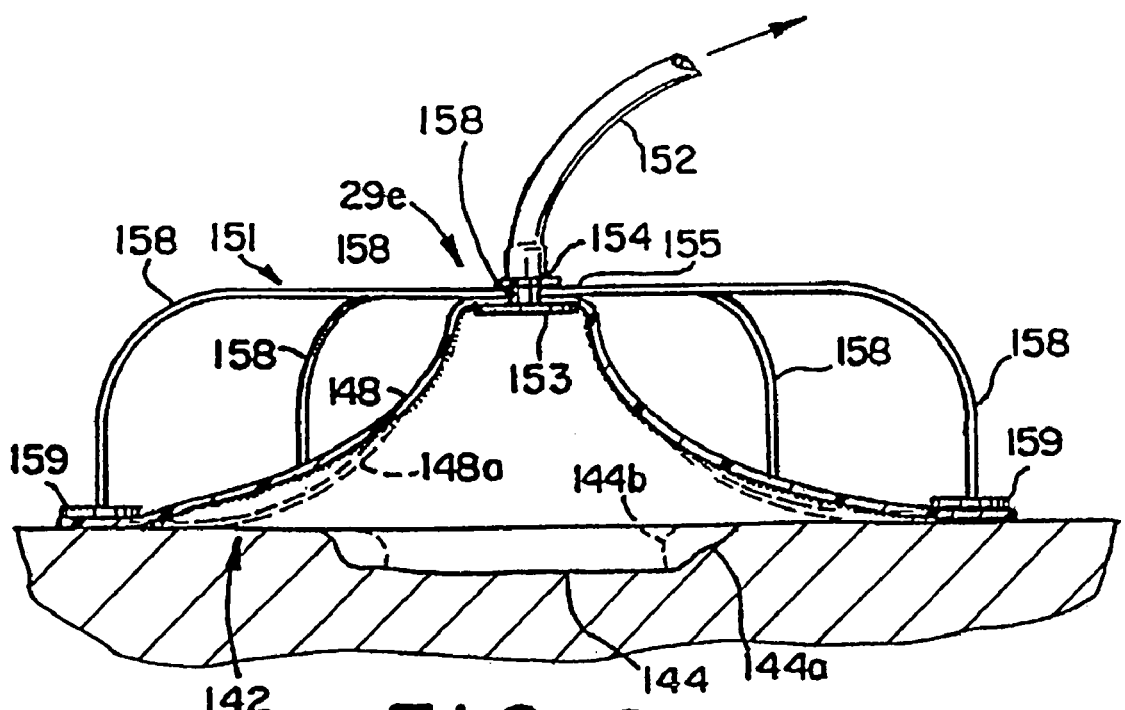
FIG. 6 is a schematic elevational view of a reduced pressure appliance, shown in partial section, having a rigid outer frame with support legs for supporting a flexible, fluid impermeable sealing cover over a wound.

For applications where a downward pressure of the appliance into a wound is not desired, a reduced pressure appliance 29e, as shown in FIG. 6, may be utilized having a support structure, generally designated 151, which is positioned external to a flexible sealing sheet 148 for covering a wound 144. The flexible cover sheet 148 is in the form of a flexible, fluid impermeable, adhesive polymer sheet. The reduced pressure appliance 29e shown in FIG. 6 includes an external support frame 151 in the form of a series of spider-like legs 158 radiating outwardly from a central support hub 155. The legs 158 hold the central hub 158 directly over the wound 144. A connector 153 is removably mounted to the hub 155 to permit a suction tube 152 to be connected with the flexible cover sheet 148. The connector 153 may screw together and apart to permit the connector to be removably mounted relative to the hub 155. The flexible adhesive sheet 148 is adhered to the connector 153 at hub 155 and to the surrounding normal skin 142 so that the sheet is suspended over the wound 144 from the hub 155 in tentlike fashion. The flexible sheet is adhesively sealed to the connector 153 at the hub 155 and is also adhesively sealed to the skin 142 around the periphery of the wound 144 to form a fluid-tight or gas-tight enclosure over the wound site. The legs 158 of the frame 153 extend radially outward from the hub 153 and stand upon feet members 159 which may rest upon the outer periphery of the sheet 148 to help hold the cover sheet 148 in a position from being sucked together during the application of suction. Alternatively, the feet members 159 may extend beyond the cover sheet 148 and may rest upon the surrounding tissue beyond the periphery of the cover sheet 148. The connector 153 supported on the hub 155 provides a suction port 154 through which suction is supplied to the appliance 29e via suction tube 152. Tube 152 is connected to a vacuum system 30 of the type previously described for supplying reduced pressure within the cover sheet 148. When suction or reduced pressure is introduced via port 154, the sheet 148 deforms inwardly and downwardly to the position shown in phantom at 148a thus developing tension which is exerted upon the surrounding skin 142. The deformed sheet in position at 148a pulls the edges of the wound 144 inwardly to the position indicated in phantom at 144b hence promoting closure of the wound 144.

Negative pressure appliances are useful for treating a variety of wounds. Treatment of a wound can be carried out by securing a negative pressure appliance to the treatment site as previously shown and described, and then maintaining a substantially continuous or cyclical reduced pressure within the appliance until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex. It may be preferable to change the appliance periodically, such as at 48 hour intervals, during treatment, particularly when using appliances incorporating a screen on or in the wound. The method is preferably practiced using a negative or reduced pressure ranging from 0.01 to 0.99 atmospheres, and more preferably practiced using a negative or reduced pressure ranging between 0.5 to 0.8 atmospheres. The time period for use of the method on a wound may preferably be at least 12 hours, but can be, for example, extended for one or more days. There is no upper limit beyond which use of the method is no longer beneficial; the method increases the rate of closure up to the time the wound actually closes. Satisfactory treatment of various types of wounds has been obtained via the use of reduced pressures equivalent to about 2 to 7 in. Hg below atmospheric pressure.

Supplying reduced pressure to the appliance in an intermittent or cyclic manner has also been demonstrated to be useful for treating wounds. Intermittent or cyclic supply of reduced pressure to an appliance may be achieved by manual or automatic control of the vacuum system. A cycle ratio, the ratio of "on" time to "off" time, in such an intermittent reduced pressure treatment may be as low as 1:10 or as high as 10:1. The preferred ratio is approximately 1:1 which is usually accomplished in alternating 5 minute intervals of reduced pressure supply and non-supply.

A suitable vacuum system includes any suction pump capable of providing at least 0.1 pounds of suction to the wound, and preferably up to three pounds suction, and most preferably up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

The present invention also includes a method of treating damaged tissue which comprises the steps of applying negative pressure to a wound for a selected time and at a selected magnitude sufficient to reduce bacterial density in the wound. Open wounds are almost always contaminated with harmful bacteria. Generally a bacterial density of $10^5$ bacterial organisms per gram of tissue is regarded as infected. It is generally accepted that at this level of infection, grafted tissue will not adhere to a wound. These bacteria must be killed, either through the wound host's natural immune response or through some external method, before a wound will close. The application of negative pressure to a wound appears to reduce the bacterial density of the wound. It is believed that this effect is due to either the bacteria's incompatibility with a negative pressure environment or the increased blood flow to the wound area, as blood brings with it cells and enzymes to destroy the bacteria. The method can be used to reduce bacterial density in a wound by at least half. More preferably, it can be used to reduce bacterial density by at least 1,000 fold. Most preferably, the method can be used to reduce bacterial density by at least 1,000,000 fold.

The present invention also includes a method of treating a burn which comprises the steps of applying negative pressure to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24–48 hours into a full thickness burn, one in which all epidermal structures are destroyed. The application of negative pressure to the wound prevents the infection from becoming sufficiently severe to cause destruction of the underlying epidermal structures. The magnitude, pattern, and duration of pressure application can vary with the individual wound.

The present invention also provides a method for enhancing the attachment of living tissue to a wound which comprises the steps of first joining the living tissue to the wound to form a wound-tissue complex, then applying a negative or reduced pressure of selected magnitude to the wound-tissue complex over an area sufficient to promote migration of epithelia and subcutaneous tissue toward the complex, with the negative pressure being maintained for a selected time period sufficient to facilitate closure of the wound. Attachment of living tissue to a wound is a common procedure that can take many forms. For example, one common technique is the use of a "flap," a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure to the wound-graft complex reduces bacterial density in the complex and improves blood flow to the wound, thereby improving the attachment of the grafted tissue. Further features of the apparatus and methods for the use thereof shall be made apparent in the following examples.

EXAMPLE 1

Treatment of Open Wounds

In order to demonstrate the use of a negative pressure appliance in the treatment of open wounds, an animal study was conducted using pigs as subjects. Pigs are frequently used as subjects in wound healing studies since they have essentially the same skin and subcutaneous tissue structure as humans.

Five 15 kg Chester pigs were obtained and acclimated for 1 week prior to use. The animals were sedated with an intramuscular injection of ketamine (25 mg/kg):xylazine (2.5 mg/kg):acepromazine (5 mg/kg). The backs and sides of the animals were shaved and scrubbed for surgery. One percent halothane was administered by endotracheal tube for maintenance of anesthesia. Two circular wounds were created on the midline of the animals. The wounds were 2.5 cm in diameter having a depth reaching, but not including, the deep fascia over the spine (approximately 1 cm). Wounds in pigs in this site do not contract during healing. Alginate impressions were made of each wound to determine the volumes of the wounds.

A reduced pressure appliance of the type discussed in connection with FIGS. 2 and 11 was positioned over each wound, and the cups were sealed to the skin with an Ioban sheet. A non-compressible silicone tube was attached to the anterior appliance of each pig and a reduced pressure of 5 in. Hg below atmospheric pressure was supplied to the anterior appliances. No reduced pressure was applied to the posterior wounds. The animals were allowed to recover from anesthesia and given food and water ad libitum. The tubes were suspended from a pulley system over the top of each pen arranged to provide each animal with full, unrestricted access to its pen.

The animals were sedated 48 hours after surgery as described above, and then daily thereafter, so that alginate impressions could be made of each wound. This routine was continued until the wounded areas were filled with granulation tissue until coplanar with the surrounding tissue. The results of this experiment, including time to complete filling of the wound space by granulation tissue and the rate of granulation tissue formation, are presented in Table 1. The data in the third column of Table 1 shows the number of days needed for the treated and non-treated wounds to heal. In order to allow comparisons between the healing rate of variously-sized wounds, the data in the fourth column is expressed as a healing rate in terms of cc granulation tissue per day. As can be seen, the treated wounds exhibited higher rates of healing than did the non-treated wounds. The wounds treated with reduced pressure filled with granulation tissue at an average rate that was 52.3% greater than the rate of granulation of the control wounds. Animals numbered 1 and 2 experienced intermittent loss of reduced pressure throughout the experiment, yet the treated wounds of these animals also healed significantly faster than their control wounds.

TABLE 1

| Animal | Wound | Initial Wound Volume (cm³) | Days to Full Granulation | Fill Rate (cm³/day) | % Rate Increase Due to Treatment |
|---|---|---|---|---|---|
| #1 | Control | 4.9 | 13 | 0.38 | |
| | Treated | 5.3 | 11 | 0.48 | 26.3 |
| #2 | Control | 7.2 | 8 | 0.90 | |
| | Treated | 9.3 | 8 | 1.16 | 28.9 |
| #3 | Control | 4.0 | 12 | 0.33 | |
| | Treated | 3.5 | 6 | 0.58 | 75.8 |
| #4 | Control | 4.7 | 11 | 0.43 | |
| | Treated | 5.0 | 7 | 0.71 | 65.1 |
| #5 | Control | 4.7 | 11 | 0.43 | |
| | Treated | 5.1 | 7 | 0.71 | 65.1 |
| Average | — | — | — | — | 52.3 |

EXAMPLE 2

Reduction of Infection

During the course of the experiment described as Example 1 above, it was observed that the reduced pressure-treated wounds were much cleaner and bled more spontaneously than non-treated wounds. It was therefore undertaken to determine the relative rates of clearance of a known bacterial inoculum from treated and non-treated wounds.

Five 15 kg pigs were obtained and wounds created as set forth in Example 1. Two 2.5 cm diameter defects were created on the dorsum of each pig using a sterile technique, with 7.5 cm interval retained between the edges of the defects. Hemostasis was obtained by electrocautery. Prior to placement of the reduced pressure appliances, $10^8$ organisms of *Staphylococcus aureus* in 1 ml saline solution were injected into each wound. The reduced pressure appliances of the type shown in FIGS. 2 and 11 were then attached as in Example 1. A reduced pressure of 5 in. Hg below atmospheric pressure was applied to one of the wounds upon each animal. Reduced pressure was not applied to the other wound upon each animal. T-shirts were placed over the animals and no antibiotics were given during the course of the study. The animals were sedated as in Example 1 at 24 hour intervals, and a 3 mm diameter full thickness biopsy was taken from each wound site daily. The devices were then reattached and reduced pressure re-applied. This routine was continued for one week.

The biopsy samples were weighed and sterile saline (99× biopsy weight) added. The tissue samples were homogenized in a tissue grinder and serial dilutions were made in triplicate. 100 microliters of each dilution was plated on a blood agar plate and incubated overnight. The number of colonies were counted on each plate and thus the number of organisms per gram of tissue was calculated. The data was recorded as the common logarithm of the number of organisms/gram tissue and is shown in Table 2.

TABLE 2

| | Average $Log_{10}$ (organisms/gm) | | | | | | |
|---|---|---|---|---|---|---|---|
| | Day 0 | Day 1 | Day 2 | Day 3 | Day 4 | Day 5 | Day 7 |
| Control | 8.44 | 8.04 | 8.17 | 7.13 | 7.13 | 8.82 | 7.08 |
| Treated | 7.69 | 7.36 | 7.37 | 6.79 | 6.43 | 3.98 | 4.32 |

As can be seen in Table 2, the common logarithm of the average number of organisms per gram of tissue present in the treated and non-treated wounds decreased slightly for all five animals over the first 4 days. In the treated wounds, the mean log of organisms/gm decreased dramatically between days 4 and 5. The mean log of organisms/gm within the non-treated wounds increased during the same period. Using the traditional baseline of $10^5$ organisms/gm to define infection, the data of Table 2 shows that the average treated wound was disinfected after four days of treatment while the average non-treated wound was still infected after 7 days.

EXAMPLE 3

Treatment of Burns

Use of reduced pressure appliances upon burns has been found to retard the progression of partial thickness burns into full thickness burns. A partial thickness burn is a burn in which the depth of cell death due to thermal trauma does not extend below the level of the deepest epidermal structures (i.e., the base of hair follicles, sweat glands, sebaceous glands, etc.). A burn that is initially a partial thickness burn will often deepen and progress into a full thickness burn due to insufficient blood circulation to the epidermal cells beneath the partial burn.

EXAMPLE 3A

The backs of five 15 kg pigs were shaved and scrubbed for surgery. A 1.5 inch diameter brass rod was heated to 190° C. in an oil bath. The rod was pressed onto the pig's skin for 15 seconds following a well-known technique of relating depth of burn to time and temperature. Three burns were created over the spine of each pig, separated by 5 cm intervals. Suction apparatus cups of the configuration shown in FIGS. 2 and 11 were placed over two of the burns, with silver sulphadiazine (Silvadine) cream, the standard antibiotic cream applied to human burns prior to excision of burned tissue, applied to the third. Cefaxolin (Kefzol) (500 mg) was administered intramuscularly (antibiotic). Suction (2–6 pounds vacuum) was applied to one of the cups. A small (2 mm) punch biopsy was taken of the wounded area and examined histologically for depth of burn.

Biopsies were analyzed by a dermatopathologist who was not told the nature of the study. It was concluded that the suctioned tissue specimens were healthier and healing more quickly than non-suctioned specimens.

EXAMPLE 3B

A set of 2 cm diameter standardized depth partial thickness burns were created by pressing a heated metal rod to each side of five anesthetized pigs to create 16 burns on each side of each pig. Reduced pressure appliances of the type shown in FIGS. 2 and 11 were secured over each of the burns on the left side of each animal and a continuous pressure of 6 in. Hg was supplied to the reduced pressure appliances. The animals were anesthetized daily, and elliptical full-thickness biopsies extending from non-injured tissue, through the center of each burn, and into non-injured tissue were harvested, fixed in formalin, processed for histological analysis and stained with Hematoxylin/eosin and Gomori's trichrome. The histologic slides were then given to a Dermatopathologist for blind determination of burn depth according to the Breslow Local Scale of maximum depth of cell death below the surface of the skin.

The Breslow Level (maximum total depth) for the burns treated by reduced pressure was 0.095 mm. The maximum depth of the burns which were not treated by reduced pressure was 0.885 mm. The use of reduced pressure appliances thus resulted in a 112% reduction in the maximum depth of burn progression.

EXAMPLE 3C

Treatment of Burn with Negative Pressure

Patient B, is admitted with second and third degree burns over the face and upper extremities, including both hands, as a result of a house fire. A large mitten-shaped reduced pressure appliance of the general type shown in FIGS. 1 and 10 is placed over the patient's right hand, with open cell foam inserts placed between the fingers to apply reduced pressure to the interdigit spaces. Three pounds of vacuum is applied cyclically in a pattern of five minutes on, 5 minutes off. The appliance is changed on a three times per week schedule. Treatment is continued until the necrotic tissue sloughs off or is excised, followed by split thickness skin graft placement.

EXAMPLE 4

Treatment of Flaps

In order to determine the effect of reduced pressure application upon skin flap survival, five 15 kg Chester pigs were obtained and acclimated for 1 week as described previously. Two dorsally-based 3 cm by 12 cm flap outlines were drawn using indelible ink on each side of the pigs, leaving 6 cm between each flap. The flaps were assigned to one of four groups as follows:

(1) Dual-treated flaps are flaps that were exposed to reduced pressure both prior to and following surgery;
(2) Pre-treated flaps are flaps that were exposed to reduced pressure prior to surgery, but were not exposed to reduced pressure after surgery;
(3) Post-treated flaps are flaps that were exposed to reduced pressure following surgery; and
(4) Control flaps are flaps that were not exposed to reduced pressure either pre- or post-surgery.

The pre-treated flaps were initially treated by covering an area surrounding one of the flap outlines on the left side of each animal with a reduced pressure appliance of the type shown in FIGS. 1 and 10 having a large piece of open cell foam into which a tube was inserted. The foam was covered and sealed to the flap area with impermeable adherent sheeting. A reduced pressure of 7 pounds was then continuously applied to the area for 7 days.

On the day of surgery, each pig was sedated as previously described and anesthesia was maintained by 1% halothane. Two 3 cm by 12 cm dorsally based flaps were created on each side of the pig following the flap outlines. The flaps were created at a depth immediately below the *panniculus carnosus* (a subcutaneous muscle layer). The flaps were raised and then sutured back in place with single, interrupted sutures of 3-0 nylon. The reduced pressure appliances were then placed over the anterior flaps on each side of the animal. A reduced pressure of 5–7 pounds was continuously applied to the anterior flaps. Each suction tube ran from the appliances on the animals upward through a pulley suspended over the pens and down to a vacuum trap bottle to collect any liquid exudate. A hose was connected from each vacuum trap bottle to a vacuum pump to supply the reduced pressure to the appliances. The animals had free access to all areas of the pen.

The animals were anesthetized 72 hours after surgery and the appliances were removed. Photographs of each side of the animals were taken, and tracings of the flaps (and encompassing any discolored areas) were made on acetate to allow for planimetric calculation of percent survival. The appliances were then replaced and reduced pressure re-applied. This routine was continued at 48 hour intervals until no further necrosis or healing of the flaps was observed.

The distal portions of all flaps were discolored 72 hours post surgery, with the flaps exposed to reduced pressure being lighter in color. The distal ends of all flaps appeared to necrose and an eschar formed over the distal portion of each flap. Over time the eschar spontaneously desquamated, exposing the outline of the original flap. The eschar over the control and pre-treated flaps consistently desquamated sooner than the post-treated and the dual-treated flaps. The control flaps had contracted to a Y shape which was evident after the eschar had desquamated. The dual-treated flaps had contracted slightly and appeared as long, thin rectangles after dislodgement of the eschar. The pre-treated flaps and post-treated flaps were intermediate between the control and dual-treated flaps in regard to flap contraction.

Dual-treated flaps exhibited the greatest survival in terms of percent retention (72.2%) of the original flap size. The post-treated flaps had the second greatest survival (67.4%). The pretreated flaps had the third most flap survival (64.8%). The control flaps had the least flap survival (51.2%). All treated flaps (dual-treated; pre-treated; and post-treated) exhibited significantly greater surface area survival than the control flaps. The dual-treated flaps had significantly greater surface area survival than either the pre-treated or post-treated flaps. The pre-treated flaps were not significantly different than post-treated flaps in regard to flap survival.

EXAMPLE 5

Treatment of Decubitus Ulcers

Application of reduced pressure was tested upon chronic decubitus ulcers and was found to be effective in the treatment thereof. Necrotic soft tissue was removed from the ulcers prior to placement upon the treatment site of a reduced pressure appliance of the type described in connection with FIGS. 1 and 10. Treatment of decubitus ulcers was tested using both continuous and cyclic application of reduced pressure. It was found that cyclic application of reduced pressure was both more effective and produced less discomfort for the patients than continuous application. Cyclic application of reduced pressure was conducted according to an application schedule of 5 minutes of suction followed by 5 minutes of non-suction. In 15 patients tested, successful treatment required from 2 to 13 weeks. Thirteen of the ulcers healed completely and every ulcer treated demonstrated progressive decrease in size during treatment. The following case histories demonstrate the manner in which various pressure sores were treated:

Case 1—A 39 year-old male T4 paraplegic had suffered from multiple recurrent pressure sores over a period of 8 years. He had been treated for a trochanteric decubitus with a tensor fascia lata flap which had developed a recurrent ulcer in the center of the flap 4 months prior to presentation. The ulcer was debrided of necrotic tissue to non-involved periosteum resulting in a wound measuring 12 cm by 5 cm with a depth of 5 cm. During the course of 4 weeks of cyclic reduced pressure application, the wound progressively closed and spontaneously re-epithelialized. Reduced pressure of 5 in. Hg below atmospheric pressure was applied cyclically with 5 minute intervals of applied pressure followed by 5 minute intervals with no applied pressure. The wound remained healed more than 5 months after treatment.

Case 2—A 45 year old male paraplegic suffered from a recurrent right ischial fosea pressure sore and abscess prior to treatment. Debridement of the wound was carried out with partial ischial resection. A week later, a re-advancement of the V-Y biceps femoris flap and rotation gluteus flap was performed. Six days later, the wound dehisced and the patient developed bilateral pneumonia requiring ventilatory support. The flap became progressively edematous and firm and resisted all efforts at mobilization. At this point, reduced pressure treatment providing continuous, non-cyclic suction or a vacuum at approximately five 5 in. Hg below atmospheric pressure was initiated. A total of 2 liters of fluid was removed by the reduced pressure appliance during the first 72 hours of treatment. Intravenous fluids were administered to replace the fluid removed from the wound. The appliance was replaced and the wound was examined three times each week. Treatment was continued for a total of six weeks during which the flap became progressively less indurated, granulation tissue formation rapidly progressed, the edges of the wound came into approximation, and the wound was healed completely.

Case 3—A 51 year-old T1 paraplegic had multiple previous pressure sores culminating in bilateral asynchronous hip disarticulations and bilateral total thigh flaps. Seven months prior to admission, he developed a 7 cm by 23 cm pressure sore over the remnants of both ischia. Bone was exposed and on tissue was available for wound closure. Dressing changes over a period of three months had failed to improve the wound. A reduced pressure appliance was then secured to the wound. During the first 3 weeks of treatment, reduced pressure of 5 in. Hg below atmospheric pressure was continuously applied. For the following 9 weeks, reduced pressure was applied cyclically in 5 minute intervals. The appliance was replaced every three days during treatment. In the course of the treatment, the wound first granulated to cover the bone completely and then the wound re-epithelialized from the margins. After 12 weeks of the treatment, a 2 cm by 5 cm scrotal flap was used to cover the midline area of the wound. The wound has remained stable beyond 6 months after treatment.

EXAMPLE 6

Treatment of Dehisced Incisions

A 50 year old debilitated white male who had undergone a colostomy through a midline laparotomy was re-admitted to the hospital for wound dehiscence and evisceration following an upper respiratory infection. He was taken immediately to the operating room and the abdominal wall was closed with Prolene mesh. Six weeks after placement of the Prolene mesh, the wound was still open and measured 28 cm by 23 cm. Only sparse granulation tissue had grown through the Prolene mesh during the six weeks. At this time a large reduced pressure appliance of the type shown in FIG. 5 was placed on an underlying porous aquaplast sheet (WFR/Aquaplast Corp., Wycoff, N.J. 07481) over top of the Prolene mesh/wound surface and the space closed with a covering tent of Ioban. A continuous vacuum of 5 in. Hg below atmospheric pressure was applied. The appliance was changed three times per week. After 8 days of treatment, granulation tissue had grown through and totally covered the Prolene mesh. Two days later, the patient was taken to the operating room, where the surrounding tissue was undermined and used to close 75% of the wound. Split thickness skin grafts were used to cover the remainder of the wound, and were placed on the bed of granulation tissue. There was 80% take of the grafts, and the remaining areas healed spontaneously with wet to dry dressing changes. The wound has remained stable 16 months after surgery.

EXAMPLE 7

Treatment of Infected Wound

Infected wounds have been successfully treated via application of reduced pressure as described in the following cases:

Case 1—A 39 year old white male sustained severe avulsive trauma to his left lower extremity in a motor vehicle accident 10 years prior to presentation. He presented with a ten year history of chronic osteomyelitis and a 3 cm diameter open ulcer with exposure of bone of his left lateral malleolus. He had previously undergone 7 local surgical procedures to attempt closure of the wound. An arteriogram demonstrated a one vessel foot with diffuse atherosclerosis and post traumatic changes. The extremity was debrided of necrotic soft tissue and all involved bone saucerized. The patient was placed on a five week course of antibiotics. The day after debridement, a reduced pressure device of the type shown in FIGS. 2 and 11 was applied over the wound and a reduced pressure of 5 in. Hg below atmospheric pressure was applied. The device was changed on a three times per week schedule. After 14 days of treatment, the wound was smaller and filled with granulation tissue which completely covered the previously exposed bone. A split thickness skin graft was placed over the wound and healed primarily. The wound has been stable for 13 months with no recurrence of osteomyelitis or tissue breakdown.

Case 2—A 51 year old white male T8 paraplegic was admitted to the hospital for an infected left trochanteric pressure sore which had been present for one year and measured 4 cm by 6 cm. The patient had previously undergone multiple procedures for treatment of this condition including a V-Y advancement flap 4 months prior to presentation. A scan revealed possible chronic osteomyelitis of the left femur. It was decided to treat the potential osteomyelitis with a five week course of IV antibiotics. The wound was debrided, then treated using a reduced pressure appliance of the type shown in FIGS. 1 and 10 for 6 weeks with cyclical reduced pressure (5 in. Hg below atmospheric pressure; 5 minutes on/5 minutes off). The wound rapidly granulated and decreased in size. After 6 weeks the wound had closed and the patient discharged. The patient was readmitted 1 month later with a draining sinus tract to the bone. The previously scanned head of the left femur was resected and the wound closed primarily over drains. The wound healed without further problems.

EXAMPLE 8

Chronic Open Wound Secondary to Stasis Ulcers

A 45 year old black female patient with a 10 year history of bilateral stasis ulcers of the pretibial area was presented with bilateral 10 cm by 15 cm infected ulcers with exposed fascia. Two previous attempts at skin grafting in the previous year had failed. The patient was treated using a reduced pressure appliance of the type shown in FIGS. 1 and 10 for 14 days with cyclical (5 minutes on/5 minutes off) reduced pressure of approximately 5 in. Hg below atmospheric pressure. After 14 days treatment, quantitative bacterial counts of both ulcers were below 102 bacteria/gram tissue, and both ulcers appeared as healthy granulating beds. Split thickness skin grafts were then applied and exhibited 100% take. The patient is ambulating, and the wounds have remained healed for 2 months, which is the longest the wounds had been healed in the last 10 years.

EXAMPLE 9

Enhancement of Blood Flow

It is believed that the efficacy of reduced pressure appliances in such treatment as have been described is due at least in part to enhancement of blood circulation within the treated wounds. In order to determine the effect of pressure application upon blood flow, a laser doppler needle probe was inserted into tissue adjacent to a pressure sore. A baseline flow level was recorded for thirty minutes. Then, the relative blood flow level was measured while a reduced pressure corresponding to 5 in. Hg below atmospheric pressure was continuously applied to the wound for 30 minutes using a reduced pressure appliance of the type shown in FIGS. 1 and 10. During continuous reduced pressure application, the relative blood flow level was only slightly higher than the baseline level.

Then the supply of reduced pressure to the appliance was cycled on and off at equal 5 minute intervals. During the "off" portions of the cycle, the relative blood flow level was twice as high as the baseline level. It is postulated that the increased blood flow during the off cycle is likely due to a "rebound" phenomenon. During the "on" cycle, blood is drawn toward the wounded tissue from both the venous and arterial branches of the vascular network in the vicinity of the wound. During the "off" cycle, this blood is transported toward the venous branch of the vascular network at a rate that is greater than would have been observed in the absence of the preceding "on" cycle.

The terms and expressions which have been employed are used as terms of description and not of limitation and there is no intention in the use of such terms and expressions of excluding any equivalents of the features shown and described, or portions thereof, but it is recognized that various modifications are possible within the scope of the claimed invention.

The invention claimed is:

1. An appliance for administering a reduced pressure treatment to a wound, comprising:
   (a) a one-piece flexible adhesive cover configured to cover and enclose the wound and adapted to maintain reduced pressure at the site of the wound;
   (b) reduced pressure supply means for connection to a source of suction, said reduced pressure supply means cooperating with said cover to supply at least 0.11 atm of reduced pressure; and
   a fluid trap interconnected between said reduced pressure supply means and said cover for collection of wound exudate.

2. The appliance as recited in claim 1 wherein said cover includes an adhesive material adapted to secure said cover to the tissue surrounding the wound.

3. The appliance according to claim 1, comprising a porous material comprising a synthetic polymer disposed within the cover and adapted to promote the formation of granulation tissue in the wound.

4. The appliance as recited in claim 3 wherein said screen comprises a porous sheet.

5. The appliance as recited in claim 3 wherein said porous material comprises a foam screen.

6. The appliance according to claim 1, wherein the reduced pressure supply means is adapted to supply at least 0.136 atm of reduced pressure.

7. The appliance according to claim 6, comprising a porous material comprising a synthetic polymer disposed within the cover and adapted to promote the formation of granulation tissue in the wound.

8. An appliance for administering a reduced pressure treatment to a wound comprising:
   (a) a flexible cover adapted to cover and enclose the wound and adapted to maintain reduced pressure at the site of the wound;
   (b) a continuous, uninterrupted adhesive seal provided on said cover adapted to seal and adhere said cover to tissue surrounding the wound;
   (c) a source of suction, cooperating with said cover to supply at least 0.11 atm of reduced pressure; and
   (d) a fluid trap interconnected between said cover and said source of suction, said trap adapted to capture wound exudate.

9. The appliance according to claim 8, wherein the suction source is adapted to supply at least 0.136 atm of reduced pressure.

10. The appliance according to claim 9, comprising a porous material comprising a synthetic polymer disposed within the cover and adapted to promote the formation of granulation tissue in the wound.

11. The appliance according to claim 8, comprising a porous material comprising a synthetic polymer disposed within the cover and adapted to promote the formation of granulation tissue in the wound.

12. An apparatus for treating a wound comprising:
   (a) a vacuum system adapted to produce a reduced pressure, wherein said vacuum system includes a collection device for collecting fluid aspirated from the wound; and
   (b) a reduced pressure appliance operably connected with said vacuum system adapted to apply said reduced pressure to the wound, the appliance including:
      a flexible cover adapted to cover and enclose the wound and adapted to maintain reduced pressure at the site of the wound;
      a porous material comprising a synthetic polymer for placement under said cover at the wound;
      an adhesive seal provided on said cover and adapted to seal and adhere said cover to tissue surrounding the wound; and reduced pressure supply means for connection with the vacuum system adapted to supply said reduced pressure within said cover to the wound.

13. The apparatus of claim 12 wherein said reduced pressure supply means comprises a length of tubing, said collection device comprises an aspirating container connected along said length of tubing between said vacuum system and cover, and said collection device comprises a flotation valve within said aspirating container for blocking said tubing when a predetermined amount of fluid is collected within said container.

14. The apparatus of claim 12 wherein said collection device comprises an expandable chamber and a sensing means for sensing expansion of said expandable chamber, said sensing means operatively connected with said vacuum system so that said reduced pressure is halted when a predetermined expansion of said expandable chamber is sensed by said sensing means.

15. The apparatus of claim 12 wherein said reduced pressure supply means comprises a length of tubing and a filter along said tubing, said filter having pores that block the supply of reduced pressure via said tubing when said pores are filled with said fluid.

16. The apparatus according to claim 5, wherein the reduced pressure supply means is adapted to maintain at least 0.136 atm of reduced pressure.

17. The apparatus according to claim 16, wherein the porous material is adapted to promote the formation of granulation tissue in the wound.

18. The apparatus according to claim 12, wherein the porous material is adapted to promote the formation of granulation tissue in the wound.

19. The apparatus according to claim 12, wherein the reduced pressure supply means is adapted to maintain at least 0.11 atm of reduced pressure.

20. A method for treating a wound, comprising:
i. locating a flexible adhesive cover over the wound to provide a chamber between the cover and the wound, said cover adapted for maintaining reduced pressure at the wound;
ii. adhesively sealing and adhering the periphery of said cover to tissue surrounding the wound;
iii. operably connecting a vacuum system with said chamber at said seal for producing said reduced pressure;
iv. interposing a fluid trap between said cover and said vacuum system; and
v. maintaining reduced pressure to promote the formation of granulation tissue at the wound until the wound has progressed toward a selected stage of healing.

21. The method according to claim 20, comprising maintaining reduced pressure of at least 0.136 atm at the wound to promote the formation of granulation tissue until the wound has progressed toward a selected stage of healing.

22. The method according to claim 21, comprising locating a porous material comprising a synthetic polymer under the cover, the porous material adapted to promote the formation of granulation tissue in the wound.

23. The method according to claim 20, comprising locating a porous material comprising a synthetic polymer under the cover, the porous material adapted to promote the formation of granulation tissue in the wound.

24. An appliance for administering a reduced pressure treatment to a wound comprising:
(a) a one-piece flexible sheet adapted to cover and enclose the wound and adapted to maintain reduced pressure at the site of the wound;
(b) a porous material comprising a synthetic polymer for placement under the sheet at the wound;
(c) an adhesive seal provided on said sheet adapted to seal and adhere said sheet to tissue surrounding the wound;
(d) a source of suction cooperating with said sheet and said seal to supply reduced pressure beneath said sheet; and
(e) a fluid trap interposed between said sheet and said source of suction, said fluid trap including a shut off for halting the application of reduced pressure when a predetermined amount of fluid is collected within said trap.

25. The appliance according to claim 24, wherein the suction source is adapted to supply at least 0.136 atm of reduced pressure.

26. The appliance according to claim 25, wherein the porous material is adapted to promote the formation of granulation tissue in the wound.

27. The appliance according to claim 24, wherein the porous material is adapted to promote the formation of granulation tissue in the wound.

28. The appliance according to claim 24, wherein the suction source is adapted to supply at least 0.11 atm of reduced pressure.

29. An appliance for administering a reduced pressure treatment to a wound comprising:
(a) a one-piece flexible cover adapted to cover and enclose the wound and to provide a vacuum chamber about the wound to maintain reduced pressure at the site of the wound;
(b) an adhesive seal provided on said cover adapted to seal and adhere said cover to tissue surrounding the wound;
(c) reduced pressure supply means for connection to a source of suction, said reduced pressure supply means cooperating with said vacuum chamber to supply said reduced pressure of at least 0.11 atm beneath said vacuum chamber, wherein said reduced pressure supply means comprises a suction port on said vacuum chamber; and
(d) a screen adapted to promote the formation of granulation tissue at the wound for placement at a location within said vacuum chamber and secured in said location by the periphery of said vacuum chamber.

30. The appliance of claim 29 wherein said screen comprises a flexible, sheet-like mesh.

31. The appliance of claim 29 wherein said seal includes a seal member at least partially overlying said cover.

32. The appliance according to claim 29, wherein the reduced pressure supply means is adapted to supply at least 0.136 atm of reduced pressure.

33. The appliance according to claim 32, wherein the seal comprises a liquid impervious seal.

34. The appliance according to claim 29, wherein the seal comprises a liquid impervious seal.

35. An apparatus for treating a wound comprising:
(a) a vacuum system adapted to produce a reduced pressure, wherein said vacuum system comprises:
i. a vacuum pump adapted to supply at least 0.11 atm of reduced pressure; and
ii. a filter for preventing said pump from venting micro-organisms aspirated from the wound; and
(b) a reduced pressure appliance operably connected with said vacuum system adapted to apply said reduced pressure to the wound, the appliance including:
a flexible cover adapted to cover and enclose the wound and adapted to maintain reduced pressure at the site of the wound;

a porous material comprising a synthetic polymer for placement under the cover at the wound;

an adhesive seal disposed about the periphery of said cover and adapted to seal and adhere said cover to tissue surrounding the wound;

reduced pressure supply means for connection with the vacuum system, wherein said reduced pressure supply means comprises a length of tubing connected between said vacuum system and said cover; and a fluid trap interposed between said cover and said reduced pressure supply means.

36. The apparatus of claim 35 wherein said filter is connected along said tubing between said pump and said fluid trap for preventing contamination of said pump.

37. The apparatus of claim 35, wherein said vacuum system comprises control means for cyclically controlling said production of reduced pressure in alternating periods of production and non-production of reduced pressure.

38. The apparatus according to claim 35, wherein the pump is adapted to supply at least 0.136 atm of reduced pressure.

39. The apparatus according to claim 38, wherein the porous material is adapted to promote the formation of granulation tissue in the wound.

40. The apparatus according to claim 35, wherein the porous material is adapted to promote the formation of granulation tissue in the wound.

41. The apparatus according to claim 35, wherein the pump is adapted to supply at least 0.11 atm of reduced pressure.

42. A method of treating a wound comprising the steps of:
i. providing a vacuum source capable of providing at least 0.11 atm of reduced pressure;
ii. locating a flexible adhesive cover over the wound, said cover having a suction port;
iii. Locating a porous material comprising a synthetic polymer under said cover at the wound;
iv. adhesively sealing and adhering the periphery of said cover to tissue surrounding the wound to form a continuous seal;
v. operably connecting said suction port with said vacuum system for producing said reduced pressure;
v. interposing a fluid trap between said suction port and said vacuum source; and
vi. maintaining reduced pressure of at least 0.11 atm at the wound until the wound had progressed toward a selected stage of healing.

43. The method of claim 42, wherein said selected stage of healing is a reduction in bacterial density in the wound by at least 50%.

44. The method according to claim 42, comprising providing a vacuum source capable of providing at least 0.136 atm of reduced pressure.

45. The method according to claim 44, wherein the porous material is adapted to promote the formation of granulation tissue in the wound.

46. The method according to claim 42, wherein the porous material is adapted to promote the formation of granulation tissue in the wound.

47. A device for promoting closure of a wound comprising:
(a) a deformable cover adapted to be placed over the wound;
(b) a porous material comprising a synthetic polymer disposed under said cover for placement at the wound;
(c) an adhesive layer on the cover adapted to form a liquid impermeable seal between said cover and tissue surrounding the wound; and
(d) reduced pressure supply means for supplying reduced pressure and adapted to maintain at least 0.11 atm of reduced pressure therein to said enclosed volume and for deforming said cover so as to exert tension upon the tissue surrounding the wound; and
(e) a fluid trap interposed between said cover and said supply means.

48. The device according to claim 47, wherein the reduced pressure supply means is adapted to supply at least 0.136 atm of reduced pressure.

49. The device according to claim 48, wherein the porous material is adapted to promote the formation of granulation tissue in the wound.

50. The device according to claim 47, wherein the porous material is adapted to promote the formation of granulation tissue in the wound.

51. A method of promoting attachment of a skin graft onto a wound, comprising the steps of:
(a) attaching the graft to the wound; and
(b) applying reduced pressure to the graft to promote blood circulation within the graft, wherein said applying step comprises the steps of:
i. placing a porous screen over the graft on the wound;
ii. locating a cover over the graft on the wound, said cover adapted for maintaining said reduced pressure at the wound, said cover having a suction port;
iii. sealing the periphery of said cover to tissue surrounding the wound;
iv. operably connecting said suction port with a vacuum system for producing said reduced pressure; and
v. interposing a fluid trap between said suction port and said vacuum source.

52. The method of claim 51 wherein the graft is a skin flap, the method comprising the steps of:
(a) applying reduced pressure to a region of skin adjacent to the wound, and
(b) forming the flap by detaching skin from said region prior to said attaching step.

53. The method of claim 51 comprising the steps of:
(a) applying reduced pressure to a region of skin for use as the skin graft; and
(b) forming the graft by detaching skin from said region.

54. An apparatus for facilitating the healing of wounds, comprising:
a flexible cover adapted to cover and enclose a wound and adapted to maintain reduced pressure at the site of the wound;
a porous material comprising a synthetic polymer disposed under said cover for placement at the wound;
a suction pump for creating a reduced pressure of at least 0.11 atm on the area of tissue including and surrounding the wound; and
a liquid impermeable adhesive seal provided on said cover adapted to seal and adhere said cover to tissue surrounding the wound reduced pressure at said wound.

55. The apparatus according to claim 54, wherein the porous material is adapted to promote the formation of granulation tissue in the wound.

56. The apparatus according to claim 54 in which said porous material comprises an open-cell polymer foam.

57. The apparatus according to claim 54 in which said porous material comprises a porous, elastic, semi-rigid member.

58. The apparatus according to claim 54, in which said seal includes a flexible sealing rim in contact with said tissue surrounding said wound.

59. The apparatus according to claim 54, in which said cover includes a flexible polymer sheet overlying said porous material, said polymer sheet having an adhesive on at least a surface facing the wound to attach and seal said polymer sheet to said surrounding tissue.

60. The apparatus according to claim 54, in which said seal includes a sealing cuff in contact with said tissue surrounding the wound.

61. The apparatus according to claim 54, in which said pump provides at least 0.11 atm of suction.

62. The apparatus according to claim 54, in which said pump provides at least 0.136 atm of suction.

63. The apparatus according to claim 54, in which said pump provides at least 14 pounds per square inch suction.

64. An apparatus according to claim 54, in which said pump operates cyclically to provide periods of application and non-application of suction.

65. An apparatus according to claim 54, in which said pump operates continuously.

66. An apparatus according to claim 54, in which said pump supplies a reduced pressure between about 0.5 and 0.99 atmospheres to the wound.

67. An apparatus according to claim 54, wherein said pump supplies a reduced pressure between about 0.3 and 0.99 atmospheres to the wound.

68. An apparatus according to claim 54, wherein said pump supplies a reduced pressure between about 0.5 and 0.8 atmospheres to the wound.

69. The apparatus according to claim 54, wherein the suction pump is adapted to maintain at least 0.136 atm of reduced pressure.

70. The apparatus according to claim 69, wherein the porous material is adapted to promote the formation of granulation tissue in the wound.

71. An apparatus for treating a wound, comprising:
 a flexible adhesive cover adapted to cover and enclose a wound and adapted to maintain reduced pressure at the site of the wound;
 a porous material comprising a synthetic polymer for placement under the cover at the wound;
 a liquid impermeable adhesive seal provided on said cover adapted to seal and adhere said cover to tissue surrounding the wound;
 a tubular member having an end extending from beneath the seal edge to a location external to said cover for supplying reduced pressure beneath the cover; and
 a fluid trap in fluid communication with said tubular member, said fluid trap including a shut off for halting the application of reduced pressure when a predetermined amount of fluid is collected within said trap.

72. The apparatus of claim 71 wherein the porous material comprises a foam section configured to overlay the wound, and wherein said first end of said tubular member is embedded within the foam section.

73. The apparatus of claim 71 including a vacuum source that supplies a reduced pressure between about 0.3 and 0.99 atmospheres to the wound.

74. The apparatus of claim 71 including a vacuum source that supplies a reduced pressure between about 0.5 and 0.99 atmospheres to the wound.

75. The apparatus of claim 71 including a vacuum source that supplies a reduced pressure between about 0.5 and 0.8 atmospheres to the wound.

76. The apparatus according to claim 71, comprising a source of suction cooperating with said cover and seal to supply reduced pressure of at least 0.11 atm beneath said cover.

77. The apparatus according to claim 76, wherein the porous material is adapted to promote the formation of granulation tissue in the wound.

78. The apparatus according to claim 71, wherein the porous material is adapted to promote the formation of granulation tissue in the wound.

79. The apparatus according to claim 71, comprising a source of suction cooperating with said cover and seal to supply reduced pressure of at least 0.136 atm beneath said cover.

80. The apparatus according to any one of claims 1 and 3–6, wherein the reduced pressure supply means comprises control means for cyclically controlling said production of reduced pressure in alternating periods of production and non-production of reduced pressure.

81. The method according to any one of claims 8 and 9–11, wherein the suction source comprises control means for cyclically controlling said production of reduced pressure in alternating periods of production and and non-production of reduced pressure.

82. The appliance according to any one of claims 12 and 16–18, wherein the reduced pressure supply means comprises control means for cyclically controlling said production of reduced pressure in alternating periods of production and non-production of reduced pressure.

83. The method according to any one of claims 20 and 21–23, wherein the reduced pressure is applied in alternating intervals of application and non-application.

84. The appliance according to any one of claims 24 and 25–27, wherein the suction source comprises control means for cyclically controlling said production of reduced pressure in alternating periods of production and non-production of reduced pressure.

85. The appliance according to any one of claims 29 and 32–34, wherein the reduced pressure supply means comprises control means for cyclically controlling said production of reduced pressure in alternating periods of production and non-production of reduced pressure.

86. The apparatus according to any one of claims 35 and 38–40, wherein the pump comprises control means for cyclically controlling said production of reduced pressure in alternating periods of production and non-production of reduced pressure.

87. The appliance according to any one of claims 42 and 44–46, wherein said reduced pressure is applied in alternating periods of application and non-application.

88. The device according to any one of claims 47 and 48–50, wherein the reduced pressure supply means comprises control means for cyclically controlling said production of reduced pressure in alternating periods of production and non-production of reduced pressure.

89. The apparatus according to any one of claims 54 and 69, 70, 55 wherein the pump comprises control means for cyclically controlling said production of reduced pressure in alternating periods of production and non-production of reduced pressure.

90. The apparatus according to any one of claims 71 and 76–78, comprising a reduced pressure supply means cooperating with the cover, the supply means comprising a control means for cyclically controlling said production of reduced pressure in alternating periods of production and non-production of reduced pressure.

91. The appliance according to claim 1, comprising a porous material comprising a synthetic polymer for placement under the cover at the wound.

92. The appliance according to claim 8, comprising a porous material comprising a synthetic polymer for placement under the cover at the wound.

93. The appliance according to any one of claims 24, 91, and 92, wherein the porous material comprises foam.

94. The appliance according to any one of claims 24, 91, and 92, wherein the porous material comprises a honeycombed sheet.

95. The appliance according to any one of claims 24, 91, and 92, wherein the porous material comprises a mesh.

96. The appliance according to any one of claims 24, 91, and 92, wherein the porous material comprises a porous sheet.

97. The appliance according to any one of claims 24, 91, and 92, wherein the porous material comprises polyethylene, polyester, or combinations thereof.

98. The apparatus according to any one of claims 12, 35, 54, and 71, wherein the porous material comprises foam.

99. The apparatus according to any one of claims 12, 35, 54, and 71, wherein the porous material comprises a honeycombed sheet.

100. The apparatus according to any one of claims 12, 35, 54, and 71, wherein the porous material comprises a mesh.

101. The apparatus according to any one of claims 12, 35, 54, and 71, wherein the porous material comprises a porous sheet.

102. The apparatus according to any one of claims 12, 35, 54, and 71, wherein the porous material comprises polyethylene, polyester, or combinations thereof.

103. The device according to claim 47, wherein the porous material comprises foam.

104. The device according to claim 47, wherein the porous material comprises a honeycombed sheet.

105. The device according to claim 47, wherein the porous material comprises a mesh.

106. The device according to claim 47, wherein the porous material comprises a porous sheet.

107. The device according to claim 47, wherein the porous material comprises polyethylene, polyester, or combinations thereof.

108. The method according to claim 20, comprising locating a porous material comprising a synthetic polymer under the cover at the wound.

109. The method according to claim 42 or 108, wherein the porous material comprises foam.

110. The method according to claim 42 or 108, wherein the porous material comprises a honeycombed sheet.

111. The method according to claim 42 or 108, wherein the porous material comprises a mesh.

112. The method according to claim 42 or 108, wherein the porous material comprises a porous sheet.

113. The method according to claim 42 or 108, wherein the porous material comprises polyethylene, polyester, or combinations thereof.

114. The method according claim 20, 42, or 108, wherein the wound consists of epithelial and subcutaneous tissue.

115. The method according claim 20, 42, or 108, wherein the wound comprises epithelial and subcutaneous tissue.

116. The method according claim 20, 42, or 108, wherein the wound comprises a pressure sore.

117. The method according claim 20, 42, or 108, wherein the wound comprises an ischemic wound.

118. The method according to claim 20, 42, or 108, wherein the selected stage of healing comprises substantial closure of the wound.

119. The method according to claim 20, 42, or 108, wherein the selected stage of healing comprises substantially filling the wound with granulation tissue.

120. The method according claim 20, 42, or 108, wherein the selected stage of healing comprises migration of epithelial and subcutaneous tissue toward the wound.

121. The method according claim 20, 42, or 108, wherein the selected stage of healing comprises re-epithelialization of at least a portion of the wound.

122. The method according claim 20, 42, or 108, wherein the selected stage of healing is a reduction in the volume of the wound by a predetermined amount.

123. The method according claim 20, 42, or 108, wherein the selected stage of healing is a reduction in the diameter of the wound by a predetermined amount.

124. The method according to claim 20, 42, or 108, wherein said selected stage of healing is a reduction in the depth of the wound by a predetermined amount.

125. The method according to claim 20, 42, or 108, wherein the step of maintaining reduced pressure comprises uniformly applying reduced pressure across at the wound bed.

\* \* \* \* \*

UNITED STATES PATENT AND TRADEMARK OFFICE
CERTIFICATE OF CORRECTION

| | | |
|---|---|---|
| PATENT NO. | : 7,216,651 B2 | Page 1 of 1 |
| APPLICATION NO. | : 09/863234 | |
| DATED | : May 15, 2007 | |
| INVENTOR(S) | : Argenta et al. | |

It is certified that error appears in the above-identified patent and that said Letters Patent is hereby corrected as shown below:

Col. 22 line 5 insert --(c)-- before "a fluid trap".
Col. 22 line 15 replace "screen" with --porous material--.
Col. 23 line 24 replace "5" with --12--.
Col. 25 line 37 replace "Locating", with --locating--.
Col. 25 line 44 replace "v" with --vi--.
Col. 25 line 46 replace "vi" with --vii--.
Col. 28 line 15 replace "apparatus", with --appliance--.
Col. 28 lines 15-16 replace "1 and 3-6" with --1, 3, 6, and 7--.
Col. 28 line 20 replace "method" with --appliance--.
Col. 28 line 23 replace "and and" with --and--.
Col. 28 line 25 replace "appliance" with --apparatus--.

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

PATENT NO.         : 7,216,651 B2
APPLICATION NO. : 09/863234
DATED                  : May 15, 2007
INVENTOR(S)        : Argental et al.

It is certified that error appears in the above-identified patent and that said Letters Patent is hereby corrected as shown below:

On Title page 2 of the patent, add -- 5,720,720 A 2/1998 Laske -- after "5,645,081 A 7/1997 Argenta et al."
On Title page 2 of the patent, add -- 4,713,052 A 12/1987 Beck -- after "4,661,093 A 04/1987 Beck et al."

On Title page 9 of the patent, append the following thirty-six references after "Cosker, T., et al., Choice of Dressing Has a Major Impact on Blistering and Healing Outcomes in Orthopaedic Patients, Journal of Wound Care, Vo. 14, No. 1, Jan. 2005, pp. 27-29":
Title Page item 56
--ALEXANDER, J.W., et al., "Clinical evaluation of epigard, a new synthetic substitute for homograft and heterograft skin," J. of Trauma, 13:374-383, (1973)
ANON., "Standard Test Methods for Water Vapor Transmission of Materials," ASTM, Designation: E 96/E 96M – 05, Published June 2005, 11 sheets, (Exhibit D-184)
BERTONE, A.L., et al., "Management of Exuberant Granulation Tissue," Veterinary Clinic of North America – Equine Practice, vol. 3, pp 551-562, (1989).
BYERS, R.M., "Clinical effects of closed suction drainage on wound healing in patients with head and neck cancer," Arch. Otolaryngol., vol. 108:723-6, (November 1982)
CESANY, P., "Suction in the Treatment of Torpid Ulcerations," Rozhledy v chirurgii, 48-9, MINC022894-MINC022898, cover sheet and pages 406-409 English abstract on page 409 (October 31, 1969)
CHARIKER/JETER, Spartanburg General Hospital Progress Notes, dated 1986, 25 pages, (Exhibit D-158)
CHINN, S.D., "Closed wound suction drainage," J. Foot Surg., vol. 24: 76-81, (Jan-Feb 1985)
DAVYDOV, Y.A., et al., "Vacuum Therapy in Treatment of Acute Purulent Diseases of Soft Tissues and Purulent Wounds," Vestnik Khirurgili (Surgeon's Herald), Medicine Publishers 1986, 5 sheets, (Exhibit P-528)
DAVYDOV, Y., et al., "Vacuum Therapy in the Treatment of Purulent Lactation Mastitis," Vestn. Khir. P. 66-70, English translation by IRC, (Sept. 1986), (Exhibit D-292)
DAVYDOV, Y., et al., "Vacuum Therapy in the Treatment of Purulent Lactation Mastitis," Vestn. Khir. Cover sheet and pages 66-70, in Russian, English abstract provided on page 70, (1986), (Exhibit D-173)
DAVYDOV, Y., et al., "Bacteriological and Cytological Assessment of Vacuum Therapy of Purulent Wounds," Vestn. Khir., 48-52, English translation by IRC, (Oct. 1988). (Exhibit D-290)
DAVYDOV, Y., et al., "Bacteriological and Cytological Assessment of Vacuum Therapy of Purulent Wounds," Vestn. Khir., cover sheet and pages 48-52, in Russian, English abstract provided on page 52, (1988), (Exhibit D-172)

UNITED STATES PATENT AND TRADEMARK OFFICE
CERTIFICATE OF CORRECTION

PATENT NO. : 7,216,651 B2
APPLICATION NO. : 09/863234
DATED : May 15, 2007
INVENTOR(S) : Argental et al.

It is certified that error appears in the above-identified patent and that said Letters Patent is hereby corrected as shown below:

EVERETTE, W.G., "Treatment of purulent wounds and fistulae with an adhesive wound irrigation device," Annals of the Royal College of Surgeons, vol. 64: 4 pages, (1981)
FOX, R., "A rapid screen for drug abuse," The Pharmaceutical Journal, 789, (1988)
HARTZ, R.R., et al., "Healing of the Perineal Wound," Arch. Surg., vol. 115, 471-474, (1980), (Exhibit D-395)
HERRMANN, L.G., et al., "The Conservative Treatment of Arteriosclerotic Peripheral Vascular Diseases: Passive Vascular Exercises (Pavaex Therapy)", Ann. Surg. 100(4): 750-760, (1934)
HILSABECK, J., "The Presacral Space as a Collector of Fluid Accumulations Following Rectal Anastomosis", American Society of Colon and Rectal Surgeons, Oct., vol. 25, no. 7: 680-684, (1980)
JOHNSON, F., "An Improved Technique for Skin Graft Placement Using A Suction Drain", Surgery, Gynecology & Obstetrics, p. 585-586, December 1984, (Exhibit D132)
LEAPER, D.J., "The Wound Healing Process," Advances in Wound Management, T.D. Turner, et al., eds., pp. 7-16, New York: John Wiley and Sons, (1986)
MCFARLANE, R., "The use of Continuous Suction Under Skin Flaps", British Journal of Plastic Surgery, Vol. 11, 1958, pp. 77-86
MEYER, W., et al., "Bier's Hyperemic Treatment," W.B. Saunders & Co., 1908 (Exhibit D246)
MIZUNO, K., "Suctioning Sponge," Arch. Opthalmol., vol. 101:294, (Feb. 1983)
MOLONEY, G., "Apposition and Drainage of Large Skin Flaps by Suction," The Australian and New Zealand Journal of Surgery, 26(3):173-179, (1957)
NIKILOV, A., "Method of treatment of postphlebitic and varicose trophic ulcers on the lower extremities by vacuum [Vacuum treatment method in postphlebitic and varicose trophic ulcers of the lower extremities]," Khirurgiia, pages 368-374, (1981)
O'LEARY, P., ed., et al., "Techniques for Surgeons," John Wiley & Sons, 2 cover sheets and pages 417-418, article by Barbara Ann Montgomery, "142: Easy Dressing of Large, Draining Abdominal Wounds Using Moisture Vapor-Permeable Film," (1985)
PARK, G.B., et al., "The Design and Evaluation of a Burn Wound Covering", Supplied by The British Library - "The Word's Knowledge", pp. 11-15, (1978)
SMITH, S.R., "Surgical drainage," Br. J. Hosp. Med., pages 308-315, (June 1985)
SPAHN/HAMAKER slide entitled, "Poor Man's Irrigation/Vacuum Dressing used since the 1970's,"(Exhibit D-135)
SVEDMAN, P., "A dressing allowing continuous treatment of a biosurface," IRCS Medical Science: Biomedical Technology; Clinical Medicine; Surgery and Transplantation, 7:221 (1979). (Exhibit D-407)
SVEDMAN, "A dressing system providing fluid supply and suction drainage used for continuous or intermittent irrigation," Ann. Plast. Surg., vol. 17, 9 pages, (August 1986)
SVEDMAN, "Irrigation treatment in split thickness skin grafting of intractable leg ulcers," Scand. J. Plast. Reconstr. Surg., vol. 19:211-213, (1985)

UNITED STATES PATENT AND TRADEMARK OFFICE
CERTIFICATE OF CORRECTION

PATENT NO.         : 7,216,651 B2
APPLICATION NO.    : 09/863234
DATED              : May 15, 2007
INVENTOR(S)        : Argental et al.

It is certified that error appears in the above-identified patent and that said Letters Patent is hereby corrected as shown below:

SVEDMAN, P., "A dressing allowing continuous treatment of a biosurface," IRCS Medical Science: Biomedical Technology; Clinical Medicine; Surgery and Transplantation, 7:221 (1979), with annotations
TAYLOR, V., "Meeting the Challenge of Fistulas & Draining Wounds", Nursing80, 1980, June, pp. 45-51
TURNER, T.D., "Semipermeable Films as Wound Dressings", Schweiz Rundsch Med. Prax., 73(30-31): 950-952, (1984)
VILJANTO, J., "Eine neue Methode zur Behandlung offener Wundflachen," Annales Chirugine et Gynaecologiae Fenniae, 60:94-100, (1972)
YUSUPOV, Yu. N., et al., 5 sheets of English translation of "Active Drainage of Wounds", Vestnik khirurgii imeni I.I. Grekova 1987,138(4), 42-46 (1987), also attached are 3 pages of English translation by BlueSky publishing entitled "Active Wound Drainage" by Usupov and Yupifanov, Vestisik Khirugii, April 42-45 (1987)--

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

PATENT NO.         : 7,216,651 C1
APPLICATION NO.    : 95/001048
DATED              : February 27, 2013
INVENTOR(S)        : Louis C. Argenta and Michael J. Morykwas Page 1 of 1

It is certified that error appears in the above-identified patent and that said Letters Patent is hereby corrected as shown below:

On the title page of the inter partes reexamination certificate, at Field Code (73) Assignee, the assignees "Kinetic Concepts, Inc., San Antonio, TX (US); KCI USA, Inc., San Antonio, TX (US); KCI Holding Company, Inc., San Antonio, TX (US); KCI Licensing, Inc., San Antonio, TX (US); KCI International, Inc., San Antonio, TX (US)" should read --Wake Forest University Health Sciences, Winston-Salem, NC (US)--.

On the title page of the inter partes reexamination certificate, at Field Code (63) Related U.S. Application Data, line 2, the date "Dec. 19, 1998" should read --Feb. 19, 1998--.

Signed and Sealed this
Thirtieth Day of April, 2013

Teresa Stanek Rea
*Acting Director of the United States Patent and Trademark Office*

(12) INTER PARTES REEXAMINATION CERTIFICATE (547th)
United States Patent
Argenta et al.

(10) Number: US 7,216,651 C1
(45) Certificate Issued: *Feb. 27, 2013

(54) WOUND TREATMENT EMPLOYING REDUCED PRESSURE

(75) Inventors: Louis C. Argenta, Winston-Salem, NC (US); Michael J. Morykwas, Pfafftown, NC (US)

(73) Assignees: Kinetic Concepts, Inc., San Antonio, TX (US); KCI USA, Inc., San Antonio, TX (US); KCI Holding Company, Inc., San Antonio, TX (US); KCI Licensing, Inc., San Antonio, TX (US); KCI International, Inc., San Antonio, TX (US)

Reexamination Request:
No. 95/001,048, May 30, 2008

No. 90/008,693, Oct. 5, 2007

Reexamination Certificate for:
Patent No.: 7,216,651
Issued: May 15, 2007
Appl. No.: 09/863,234
Filed: May 23, 2001

Certificate of Correction issued Jun. 26, 2007.
Certificate of Correction issued Sep. 16, 2008.

( * ) Notice: This patent is subject to a terminal disclaimer.

Related U.S. Application Data

(63) Continuation of application No. 09/026,353, filed on Dec. 19, 1998, now Pat. No. 7,198,046, which is a continuation of application No. 08/467,243, filed on Jun. 6, 1995, now abandoned, which is a continuation of application No. 08/028,677, filed on Mar. 9, 1993, now Pat. No. 5,636,643, which is a continuation-in-part of application No. 07/792,001, filed on Nov. 14, 1991, now Pat. No. 5,645,081.

(51) Int. Cl.
*A61B 19/00* (2006.01)

(52) U.S. Cl. .......................................... 128/897; 602/42
(58) Field of Classification Search .................. None
See application file for complete search history.

(56) References Cited

To view the complete listing of prior art documents cited during the proceedings for Reexamination Control Numbers 95/001,048 and 90/008,693, please refer to the USPTO's public Patent Application Information Retrieval (PAIR) system under the Display References tab.

*Primary Examiner* — Beverly M. Flanagan

(57) ABSTRACT

A method of treating tissue damage comprises applying a negative pressure to a wound sufficient in time and magnitude to promote tissue migration and thus facilitate closure of the wound. The method is applicable to wounds, burns, infected wounds, and live tissue attachments. A wound treatment apparatus is provided in which a fluid impermeable wound cover is sealed over a wound site. A screen in the form of an open-cell foam screen or a rigid porous screen is placed beneath the wound cover over the wound. A vacuum pump supplies suction within the wound cover over the treatment site.

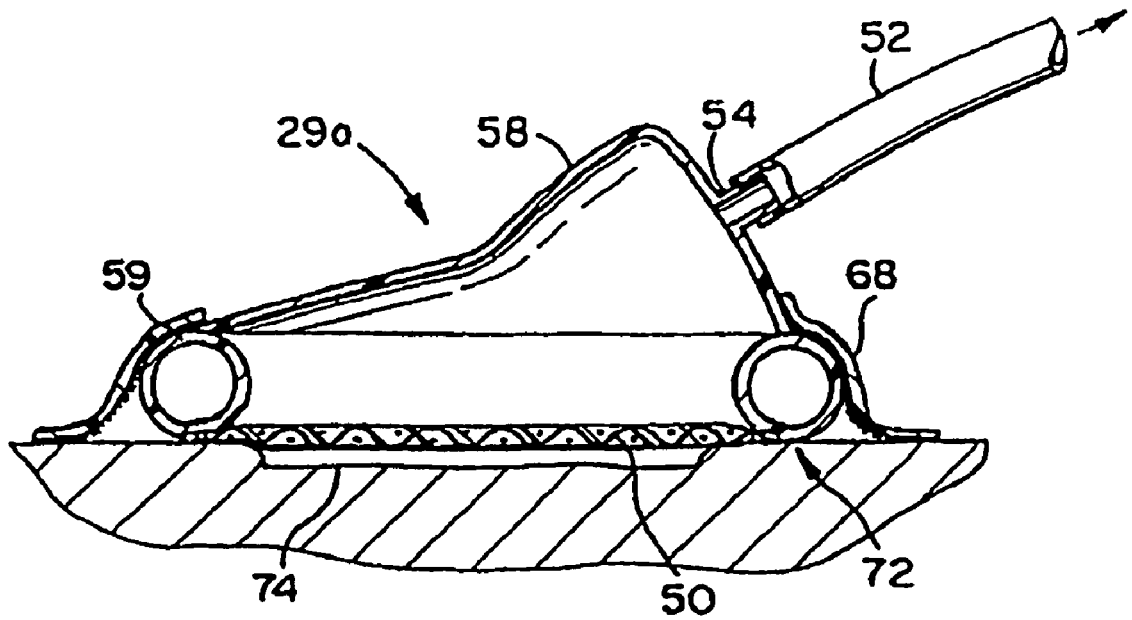

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-125 is confirmed.

* * * * *